United States Patent
Nam et al.

(10) Patent No.: US 12,109,620 B2
(45) Date of Patent: Oct. 8, 2024

(54) PLASMONIC NANOPARTICLES WITH INTRA-NANOGAP PRODUCED BY DEALLOYING, METHOD FOR PREPARING THE SAME AND USE THEREOF

(71) Applicants: SEOUL NATIONAL UNIVERSITY R&DB FOUNDATION, Seoul (KR); BIONANO HEALTH GUARD RESEARCH CENTER, Daejeon (KR)

(72) Inventors: Jwa-Min Nam, Seoul (KR); Minho Kim, Seoul (KR); Sung Min Ko, Seoul (KR)

(73) Assignees: Seoul National University R&DB Foundation, Seoul (KR); Bionano Health Guard Research Center, Daejeon (KR)

( * ) Notice: Subject to any disclaimer, the term of this patent is extended or adjusted under 35 U.S.C. 154(b) by 1106 days.

(21) Appl. No.: 16/961,174

(22) PCT Filed: Jan. 10, 2019

(86) PCT No.: PCT/KR2019/000411
§ 371 (c)(1),
(2) Date: Sep. 29, 2020

(87) PCT Pub. No.: WO2019/139383
PCT Pub. Date: Jul. 18, 2019

(65) Prior Publication Data
US 2021/0023626 A1 Jan. 28, 2021

(30) Foreign Application Priority Data
Oct. 1, 2018 (KR) .................. 10-2018-0003556

(51) Int. Cl.
*B22F 9/24* (2006.01)
*B22F 1/054* (2022.01)
(Continued)

(52) U.S. Cl.
CPC .............. *B22F 9/24* (2013.01); *B22F 1/054* (2022.01); *B22F 1/102* (2022.01); *B22F 1/17* (2022.01);
(Continued)

(58) Field of Classification Search
None
See application file for complete search history.

(56) References Cited

U.S. PATENT DOCUMENTS

| 2010/0245817 A1 | 9/2010 | Park et al. |
| 2011/0124008 A1 | 5/2011 | Nam et al. |

(Continued)

FOREIGN PATENT DOCUMENTS

| EP | 2 645 104 | 10/2013 |
| EP | 2 717 052 | 4/2014 |

(Continued)

OTHER PUBLICATIONS

Kim, "Synthesis and Catalytic/Optical Properties of Dealloying-Based Porous Nanoparticle and Plasmonic Nanogap Nanoparticle", Thesis, Seoul National University, Aug. 2017, 166 sheets.

*Primary Examiner* — George Wyszomierski
(74) *Attorney, Agent, or Firm* — HOVEY WILLIAMS LLP

(57) ABSTRACT

The present invention relates to a method for preparing a core-gap-shell nanoparticle having an average height of 0.1 nm to 10 nm, in which a Raman-active material is disposed between a core and a shell, and more specifically, to a method for preparing a core-gap-shell nanoparticle, which comprises introducing a shell made of an alloy of a second metal and a third metal, on the core particles of the first metal, the surface of which is modified with a Raman-active material; selectively removing the second metal by treating with a second metal etchant, followed by dealloying; the (Continued)

core-gap-shell nanoparticle prepared by the above method comprising a Raman-active material disposed in the gap, and uses of the core-gap-shell nanoparticle for biosensing and/or bioimaging.

8 Claims, 15 Drawing Sheets

Specification includes a Sequence Listing.

(51) Int. Cl.
| | | |
|---|---|---|
| *B22F 1/102* | (2022.01) | |
| *B22F 1/17* | (2022.01) | |
| *B82Y 5/00* | (2011.01) | |
| *B82Y 10/00* | (2011.01) | |
| *B82Y 30/00* | (2011.01) | |
| *B82Y 40/00* | (2011.01) | |

(52) U.S. Cl.
CPC ................ *B82Y 5/00* (2013.01); *B82Y 10/00* (2013.01); *B82Y 30/00* (2013.01); *B82Y 40/00* (2013.01)

(56) References Cited

U.S. PATENT DOCUMENTS

| | | | | |
|---|---|---|---|---|
| 2012/0057165 | A1* | 3/2012 | Natan | G01N 33/532 |
| | | | | 356/445 |
| 2013/0029360 | A1* | 1/2013 | Suh | G01N 33/54373 |
| | | | | 977/773 |
| 2014/0113283 | A1* | 4/2014 | Suh | G01N 21/658 |
| | | | | 435/7.1 |
| 2014/0241992 | A1* | 8/2014 | Yeh | A61K 49/0093 |
| | | | | 427/2.12 |
| 2015/0320895 | A1* | 11/2015 | Sun | A61N 5/1077 |
| | | | | 424/1.29 |
| 2016/0377549 | A1* | 12/2016 | Kang | B82Y 40/00 |
| | | | | 356/301 |

FOREIGN PATENT DOCUMENTS

| | | |
|---|---|---|
| KR | 10-2010-0109264 | 10/2010 |
| KR | 10-2011-0066881 | 6/2011 |
| KR | 20120056024 | 6/2012 |
| KR | 20130124182 | 11/2013 |
| KR | 20140029504 | 3/2014 |
| KR | 10-2016-0137099 | 11/2016 |
| KR | 20170070351 | 6/2017 |
| WO | 2017-099313 | 6/2017 |
| WO | 2017/164822 | 9/2017 |

* cited by examiner

PLASMONIC NANOPARTICLES WITH INTRA-NANOGAP PRODUCED BY DEALLOYING, METHOD FOR PREPARING THE SAME AND USE THEREOF

SEQUENCE LISTING

The instant application contains a Sequence Listing which has been submitted electronically in ASCII format and is hereby incorporated by reference in its entirety. The ASCII copy, created on Sep. 29, 2020, is named 40238_00601_ (OPA18606-US) SL.txt and is 1,586 bytes in size.

TECHNICAL FIELD

The present invention relates to a method for preparing a core-gap-shell nanoparticle having a hallow space with an average height of 0.1 nm to 10 nm between a core and a shell, in which a Raman-active material is disposed; and specifically, relates to a method for preparing a core-gap-shell nanoparticle, which includes introducing a shell, which is made of an alloy of a second metal and a third metal, on the core particles of the first metal, the surface of which are modified with a Raman-active material, selectively removing the second metal by treating with a second metal etchant, and dealloying. In addition, the present invention relates to a core-gap-shell nanoparticle, which is prepared by the above method and which comprises a Raman-active material disposed in the gap, and uses of the core-gap-shell nanoparticle for biosensing and/or bioimaging.

BACKGROUND ART

Plasmonic nanostructures, in particular, plasmonically coupled and enhanced nanogap structures, are very important due to their strong and tunable optical properties and potential application in various fields (e.g., catalysts, sensing, and imaging). Since the optical properties of plasmonic nanostructures are heavily dependent on various nanostructural properties, in order to obtain controllable, quantifiable plasmonic signals from these nanostructures, a highly precise method of synthesizing plasmonic nanostructures with high yield is required. Among many plasmonically enhanced optical signals, surface-enhanced Raman scattering (SERS) is receiving much attention due to its ultra-high sensitivity, capable of extending to the single-molecule level, along with its multiplexing potential. In this regard, SERS-based techniques are widely used in plasmonics and analytical applications (e.g., biosensing and detection of chemical agents). In plasmonics, it is well known that the extinction of localized surface plasmon resonance (LSPR) in nanoparticles (NP) of a noble metal (e.g., gold and silver) can significantly increase and localize electromagnetic (EM) field at a specific location between NPs, called "hot spots". As such, many attempts have been made to design and prepare SERS-active structures using morphology-controlled noble metal nanostructures (e.g., nanotips, nanopores, and nanoscale roughened surfaces). In particular, with respect to SERS, the electromagnetic field can be significantly enhanced through plasmon coupling in gaps or junctions between metallic nanostructures. However, the plasmon coupling in these gaps is significantly influenced by the interparticle distance and consequently has a significant effect on SERS signals. This can impart untunable reproducibility to SERS signals, which becomes a major obstacle to the common usefulness of these SERS-active structures. As a result, the development of high-precision nanometer-scale or sub-nanometer-scale gap engineering for large-scale production of these structures is an important challenge to generate reproducible and reliable SERS signals from these particles.

Among many plasmonic nanogap structures, intra-nanogap structures with a nanometer-scale internal gap can generate a strongly enhanced and tunable SERS signal due to the uniformity and tunability of the nanogap in multiple particles, and thus, they can be an effective SERS substrate. In order to form a SERS-active intra-nanogap structure, various synthetic strategies are being adopted. In particular, the introduction of thiolated DNA on AuNPs has made it possible to promote the formation of a 1 nm intra-gap during the Au—Au core-shell formation process, prepare Au nano-bridge-coupled nanogap particles (Au-NNPs) having a uniform 1 nm intra-gap with high yield, and further, to provide a strong, stable, and reproducible SERS signal. Different approaches for forming intra-nanogap structures are being adopted for synthesis of various intra-nanogap structures (e.g., a silica-interlayered nanogap structure (Au nano-Matryoshka) including a Au core and a Au shell; and a polymer or small molecule-interlayered plasmonic nanogap structure). However, all of these structures still have many shortcomings and challenges to resolve, such as complicated synthetic complexity, time and cost, reaction conditions including temperature, nanometer-scale structural precision, limits in large-scale production, particle stability, structural and compositional versatility, lack of practicality, etc. The necessity of intercalation to form intra-nanogaps inside particles and the laser polarization-dependent changes in optical signals from the intra-nanogap particles significantly limit the understanding and tuning of the plasmonic properties of these nanostructures, including the intensity and distribution of the electromagnetic field. Studies on the use and beneficial properties of these intra-nanogap particles for biomedical applications are not active, and no significant results have been obtained therefrom.

DISCLOSURE

Technical Problem

The present inventors have made extensive efforts to discover nanoparticles with a core-gap-shell structure, which have a nanogap inside the particles without an interlayer (e.g., DNA, etc.) and include a Raman-active material disposed in the above gap which is thus capable of exhibiting a significant SERS effect, and a method for preparing the nanoparticles that can be performed in a mild condition (e.g., a room temperature condition). As a result, they have confirmed that core-gap-shell nanoparticles having a nanogap in the form of a hollow space, in which a Raman-active material is disposed inside the particles, can be synthesized in high yield through selective-interdiffusive dealloying (SID) by introducing a shell made of an alloy of two different kinds of metals onto a core particle, a surface of which is modified with a Raman-active material; selectively removing one of the two kinds of metals by allowing them to come into contact with an etchant which selectively dissolves one of the two kinds of metals; and dealloying, thereby completing the present invention.

Technical Solution

To achieve the above objects, an aspect of the present invention provides a method for preparing core-gap-shell nanoparticles having a hollow space with an average height of 0.1 nm to 10 nm between a core and a shell, in which a Raman-active material is disposed, comprising: a first step of preparing first metal core particles, a surface of which is modified with the Raman-active material; a second step of adding solutions, which comprise a second metal precursor, a base, and a third metal precursor, respectively, and a solution of a reducing agent to the surface-modified first metal core particles to form an alloy shell of the second metal and the third metal; and a third step of selectively removing the second metal by treating nanoparticles of (the first metal core, the surface of which is modified with the Raman-active material)—(the second metal and third metal alloy shell) with a second metal etchant; followed by dealloying, wherein the first metal has a higher reduction potential compared to the second metal.

Another aspect of the present invention provides a nanoparticle which is a core-gap-shell nanoparticle showing a surface-enhanced Raman scattering (SERS) signal and having a hollow space between a core and a shell, in which a Raman-active material with an average height of a few nanometers is disposed, wherein the nanoparticle comprises a gap, which is a hollow space formed between a core and a shell, by selectively removing all or part of a second metal from the core made of a first metal and a shell made of an alloy of the second metal and a third metal; wherein, in the shell made of the alloy of the second metal and the third metal, the content of the second metal with respect to that of the third metal decreases progressively from the surface of the first metal core outward; and wherein the finally formed core-gap-shell nanoparticle maintains the gap through one or more metal bridges, which connect the core and the shell, comprising the second metal, the third metal, or both thereof.

Still another aspect of the present invention provides a composition for biosensing or bioimaging, which comprises the above core-gap-shell nanoparticle.

Advantageous Effects

The method of the present invention for preparing core-gap-shell nanoparticles using selective-interdiffusive dealloying (SID), unlike the conventional method of introducing an interlayer, can form within particles a nanogap with a uniform thickness controlled to be within a few nanometers without an inserted material. The core-gap-shell nanoparticles prepared by introducing a Raman-active material to the nanogap show significant SERS signals, and thus can be effectively used for ultrasensitive biosensing and/or bioimaging.

BRIEF DESCRIPTION OF DRAWINGS

In FIG. 3, A schematically illustrates a selective-interdiffusive dealloying (SID)-based strategy for the synthesis of Au—Ag dealloyed intra-nanogap particles (DIPs) from the Au/Au—Ag core/alloy shell (CAS) NPs (a proposed mechanism of the SID reaction is shown in the dotted box). In FIG. 3, B to J show TEM images of the synthesized NPs, results of EDX elemental mapping, and EDX line scan profiles across the center of the NPs (in which B to D of FIG. 3 show the results with respect to CAS NPs). In FIG. 3, E to G show the results with respect to DIPs; and In FIG. 3, H to J show the results with respect to gapless Au—Au core-shell NPs. Ag atoms were mainly located near the Au core in CAS NPs (the dotted box in D of FIG. 3), and the number of Ag atoms decreased in the vicinity of the Au core after the dealloying reaction (the dotted box in G of FIG. G), resulting in the formation of intra-nanogap. In the gapless AuNPs, an intra-nanogap was not observed (the dotted box in J of FIG. J). The EDX map of Ag shown in I of FIG. I shows noise-level signals. The white scale bars indicate 50 nm. In FIG. 3, K shows a graph illustrating the nanogap size, shell thickness, and particle size distributions of DIPs (analysis of HR-TEM images of 100 particles). In FIG. 3, L shows a TEM image of DIPs. In particular, the d-spacing of 0.235 nm for adjacent lattice fringes corresponds to the (111) plane of a face-centered cubic structure. The inset shows a ring-shaped SAED pattern of a DIP, which indicates the presence of a polycrystalline structure therein.

In FIG. 7, A shows the structural changes in DIPs with an increase in the amount of $Fe(NO_3)_3$ added. As the dealloying reaction progressed, an intra-nanogap developed gradually. In FIG. 7, B shows a graph illustrating the intra-nanogap formation-dependent changes in SERS intensity of DIPs. The solution-based SERS intensity increased with the formation of a complete intra-nanogap and was maximized at higher $Fe(NO_3)_3$ concentrations (15 mM or higher), indicating that the dealloying reaction was completed. SERS intensity of DIPs corresponded to 6 times that of CAS NPs. This indicates that the SERS enhancement was due to the strong localized electromagnetic field generated in the intra-nanogap. In FIG. 7, C shows the intra-nanogap formation-dependent UV-Vis spectra of DIPs. The extinction peak changed slightly as the dealloying reaction progressed. Due to the dealloying reaction, a new extinction shoulder peak appeared at about 660 nm (5 mM), indicating the formation of an intra-nanogap. This peak was slightly red-shifted to about 700 nm and was gradually stabilized (20 mM) after the formation of a complete and symmetric intra-nanogap.

In FIG. 8, A shows the UV-Vis spectra of as-synthesized NPs. The inset shows the colors of the NP solutions. In FIG. 8, B shows simulated extinction spectra of DIPs containing various metal compositions in the intra-nanogap. In the corresponding model, the intra-nanogap region was filled with a mixture of metal residues and water. In FIG. 8, C and D show the calculated near-field electromagnetic field (EM field) distributions of DIPs with different compositions of metal residues within the intra-nanogap [In FIG. 8, C: 12.5 mol %; and D: 0 mol %]. The excitation laser wavelength is 633 nm, and the scale bar is 20 nm.

In FIG. 14, A shows a schematic diagram illustrating SERS-based target-specific cell imaging using cRGD-modified DIP nanoprobes. In FIG. 14, B and C each show a bright field microscopic image (left) and a SERS map (right) of U87MG cells (B; high expression of integrin $\alpha_v\beta_3$) and MCF-7 cells (C; integrin $\alpha_v\beta_3$-negative), which were each incubated with the cRGD-functionalized DIP. The scale bar is 10 μm. The SERS intensities at each mapping pixel (2 μm×2 μm) were integrated for SERS spectra ranging from 983 cm$^{-1}$ to 1,023 cm$^{-1}$ shaded in D of FIG. 14 and then color-scaled for cell imaging. All of the spectra were obtained with an acquisition time of one second using a 785 nm excitation laser (4 mW laser power). In FIG. 14, D shows the SERS spectra obtained from the numerically marked positions in B and C of FIG. 14. In FIG. 14, E shows a time-dependent Raman profile of the cRGD-functionalized DIPs in cells measured within the gray box of B of FIG. 14. In FIG. 14, F and G each show a SERS map of U87MG cells which were incubated with the cRGD-functionalized DIPs and the cRGD-functionalized AuNPs (average particle diameter: 80 nm), respectively. The scale bar is 10 μm. The SERS intensities at each mapping pixel (2 μm×2 μm) were integrated for SERS spectra ranging from 983 cm$^{-1}$ to 1,023

Figure 14:
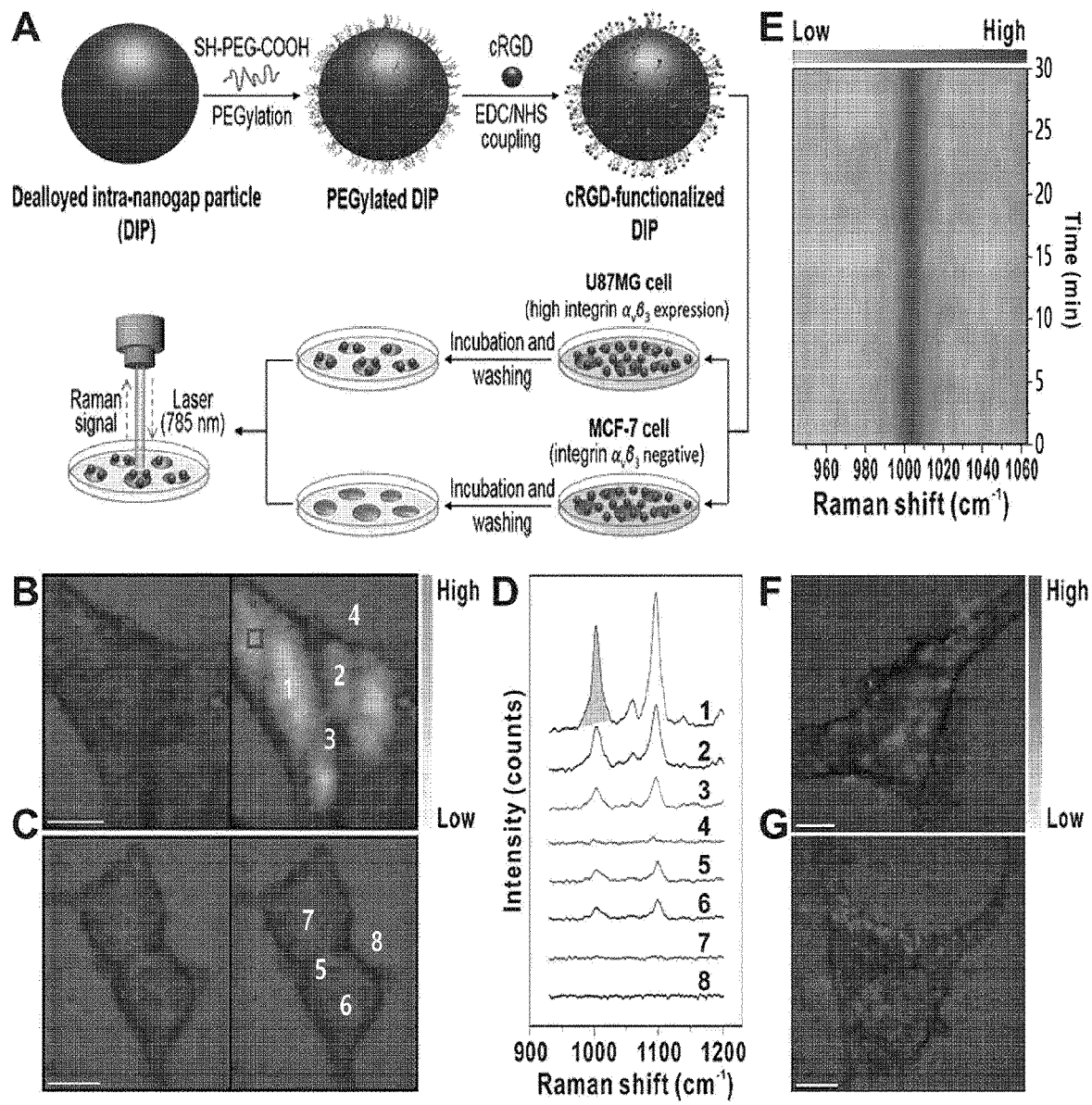
FIG. 14 shows drawings illustrating SERS-based integrin $\alpha_v\beta_3$-specific cell imaging using peptide-functionalized DIPs.

$cm^{-1}$, shaded in FIG. 14, D and then color-scaled for cell imaging. All of the spectra were obtained with an acquisition time of one second using a 633 nm excitation laser (400 µW laser power).

Figure 15:
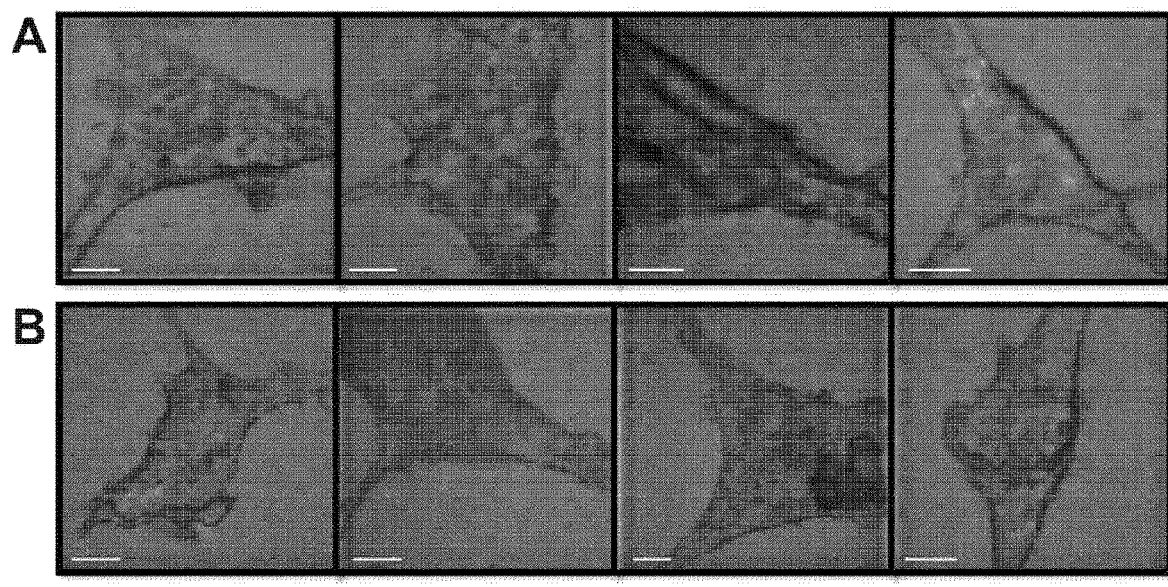

FIG. 15 shows drawings illustrating the SERS maps of U87MG cells incubated with cRGD-functionalized different imaging probes, in which FIG. 15, A shows the results for DIPs and B shows the results for AuNPs (average diameter: 80 nm). The scale bar is 10 µm. The SERS intensities at each mapping pixel (2 µm×2 µm) were integrated for SERS spectra ranging from 983 $cm^{-1}$ to 1,023 $cm^{-1}$ shaded in FIG. 14, D and then color-scaled for cell imaging. All of the spectra were obtained with an acquisition time of one second using a 633 nm excitation laser (400 µW laser power).

BEST MODE FOR CARRYING OUT THE INVENTION

To achieve the above objects, one aspect of the present invention provides a method for preparing core-gap-shell nanoparticles having a hollow space with an average height of 0.1 nm to 10 nm between a core and a shell, in which a Raman-active material is disposed. Specifically, the method of the present invention comprises: a first step of preparing first metal core particles, a surface of which is modified with the Raman-active material; a second step of adding solutions, which comprise a second metal precursor, a base, and a third metal precursor, respectively, and a solution of a reducing agent to the surface-modified first metal core particles to form an alloy shell of the second metal and the third metal; and a third step of selectively removing the second metal by treating nanoparticles of (the first metal core, the surface of which is modified with the Raman-active material)—(the second metal and third metal alloy shell) with a second metal etchant; followed by dealloying, wherein the first metal can be selected to have a higher reduction potential compared to the second metal.

The present invention is based on the establishment of conditions which enable the formation of a nanogap having a hollow space in a place where a second metal is removed (i.e., a place from the vicinity of the first metal core to a shell layer where the third metal is distributed in a large amount) in the preparation of particles having a structure of (a first metal)—(a nanogap with a hollow space)—(a third metal shell) without an interlayer, by the formation of a shell using an alloy, made of a second metal and a third metal, that can be reduced faster on the surface of the core particles of the first metal than on the surface of the core particles of the third metal, and by using an etchant that can selectively remove the second metal. The prerequisite to achieve the establishment of the above conditions is to form an alloy having a content gradient in such a manner that the second metal is reduced faster when the shell made of an alloy of the second metal and the third metal is formed so that the content of the second metal in the vicinity of the first metal core can be higher and the content of the third metal can be increased as the preparation proceeds from the innermost to the outermost of the shell. In this regard, the establishment of the above conditions may be achieved by a method of increasing the initial reaction rate by promoting the access to the second metal using the difference in reduction rate according to the difference in reduction potential, or by a method of modifying the first metal core with a material having a high binding affinity for the second metal even when the reduction potential is somewhat low.

The first metal to the third metal may each independently be a metal such as gold, silver, copper, aluminum, platinum, palladium, etc., but these metals are not limited thereto. However, as described above, for the first and second metals, it is preferable to select a combination of metals in which the first metal has a higher reduction potential; and for the second and third metals, it is preferable that the second metal be reduced faster on the surface of the first metal core in the reduction reaction of the second step, so that the second metal and the third metal have a concentration gradient in the shell. In this regard, for the second and third metals, it is possible to select a metal having a reduction tendency (i.e., reduction potential) higher than the third metal as the second metal; or to select a method in which the introduction and initial reduction of the second metal are promoted by modifying the surface of the first metal core with a material selectively having a higher binding affinity for the second metal.

For example, the second step may be performed in the presence of a base. When the second step is performed in a base-free condition, the reduction rate becomes slow due to the low pH of the solution, and it may be difficult for the second and third metals on the core to form a synthetic phase smoothly; further, it is possible that impurities that may be generated during alloy formation may be incorporated into the shell due to co-precipitation of by-products. In addition, it may be difficult to obtain a structure in which the content of the second metal is high in the shell (i.e., the vicinity of the core) of a desired composition and the content of the third metal increases as it proceeds from the innermost to the outermost of the shell. For example, when silver is used as the second metal, precipitation of silver chloride (AgCl) may occur from the reaction of the second step in the absence of a base; however, the by-products being generated can be effectively removed by lowering the pH by adding a base thereto. As the base, ammonium hydroxide ($NH_4OH$), sodium hydroxide (NaOH), potassium hydroxide (KOH), etc. may be used, but the base is not limited thereto, and the kind of the base is not limited as long as it can increase the pH of the reaction solution to an appropriate level by adding it in the second step.

For example, before the second step, a step of treating the surface-modified first metal core particles with a polymer solution having a functional group with a higher binding affinity for the second metal compared to the third metal may be further included. By the treatment of the polymer solution, the initial reduction rate of the second metal can proceed faster than that of the third metal based on the binding affinity between the polymer and the second metal, and thereby a non-uniform shell can be formed which has a composition gradient, in which a large amount of the second metal is present in a region close to the core of the shell and the content of the third metal increases as the content proceeds to the outside of the shell. Specifically, the polymer solution may include polyvinylpyrrolidone, but is not limited thereto. For example, the pyrrolidone in polyvinylpyrrolidone can interact with silver ions with a higher binding affinity than gold, and thus, it can allow silver ions to be reduced faster around the core, even though gold ions have a higher standard reduction potential (i.e., a higher reduction tendency).

The amount of the second metal precursor used in the second step can be determined complementarily by considering the amount of the third metal precursor used in the same step. For example, the amount of the second metal used can determine the thickness of the nanogaps that are subsequently formed, and the amount of the third metal used can affect the thickness of the shell. Meanwhile, even when the amount of the third metal is the same as that of the second metal, when the distribution of the third metal becomes far from the center due to a large core size or a large amount of use of the second metal, the thickness of the shell formed by the third metal may become relatively thin.

For example, the second metal and the third metal precursor may be used in an atomic % ratio of 1:0.3 to 1:10, specifically, 1:0.4 to 1:8, and more specifically 40:60 to 10:90, but the atomic % ratio is not limited thereto. For example, when the amount of the second metal used exceeds three times the number of moles of the third metal, the shell may be formed incompletely, and the gap between the formed nanogaps may be wider than the desired level, making it difficult to achieve an efficient Raman signal enhancement effect, or it may be difficult to maintain a metal bridge capable of maintaining the gap as a hollow space due to excessive etching, and thereby, the structure of the nanogap-shell may collapse. In contrast, when the ratio of the second metal precursor is as low as less than 10%, it may be difficult to form a sufficient gap to exhibit an efficient Raman signal enhancement effect.

For example, it may be possible that both the first metal and the third metal are gold and the second metal is silver. Accordingly, the core-gap-shell nanoparticles that are finally produced are gold-silver alloy shells made of gold containing some silver in the core, and the core and the shell are connected by a nanobridge made of gold, silver, or an alloy of gold and silver, and can maintain the nanogap as a hollow space formed therebetween. In addition, gold and silver are representative materials well known for exerting excellent SERS effects.

As described above, when gold is selected as the third metal and silver as the second metal, gold ions, due to their higher standard reduction potential compared to that of silver ions, exhibit a higher reduction tendency and a faster reduction rate compared to silver ions. However, in the preparation method of the present invention, a fast reduction can be induced at the early stage of the reduction reaction by inducing the access of the second metal (i.e., silver ions) to the surface of the core particles, by treating the core particles with the second metal (i.e., polypyrrolidone containing pyrrolidone that exhibits a higher binding affinity for the second metal (i.e., silver ions)) before the second step, and accordingly, a shell can be formed such that the content of the second metal (i.e., silver ions) is high around the core and the content of the third metal (i.e., gold ions) increase as the preparation proceeds to the outside.

For example, as an etchant for the second metal, ferric nitrate ($Fe(NO_3)_3$) may be used, but the etchant for the second metal is not limited thereto, and any material that can selectively dissolve the second metal in the alloy of the second metal and the third metal can be used without limitation. As a specific example, the silver in the alloy of gold and silver can be selectively dissolved and removed using ferric nitrate as an etchant.

Meanwhile, as described above, the shell of the particles prepared according to the preparation method of the present invention is characterized in that the content of the second metal is high around the core, and the content of the third metal tends to increase as the preparation proceeds to the outside of the shell. Accordingly, the dealloying of the third step begins to dissolve the second metal atoms exposed on the outer surface of the shell when they are brought into contact with the etchant, pinhole-like vacancies are formed, through which the etchant diffuses into the shell and selectively removes the second metal inside of the shell, and thereby a gap in the form of a hollow space can be formed between the core and the shell. At this time, the remaining gold and/or silver may form a bridge and a shell which connect the core and the shell and support the hollow space.

As used herein, the term "Raman-active material" refers to a material which can be detected by Raman spectroscopy, and it includes organic or inorganic molecules, atoms, complexes or synthetic molecules, dyes, naturally occurring dyes (e.g., phycoerythrin, etc.), organic nanostructures (e.g., C60, etc.), buckyballs, carbon nanotubes, quantum dots, organic fluorescent molecules, etc. Specifically, examples of the Raman-active material include mercaptobenzoic acid, aminothiophenol, FAM, Dabcyl, tetramethyl rhodamine-5-isothiocyanate (TRITC), malakit green isothiocyanate (MGITC), X-Rhodamine-5-isothiocyanate (XRITC), 3,3-diethylthiadicarbocyanine iodide (DTDC), tetramethyl rhodamine isothiol (TRIT), 7-nitrobenz-2-1,3-diazole (NBD), phthalic acid, terephthalic acid, isophthalic acid, para-aminobenzoic acid, erythrosine, biotin, digoxigenin, 5-carboxy-4',5'-dichloro-2',7'-dimethoxy, fluorescein, 5-carboxy-2',4', 5',7'-tetrachlorofluorescein, 5-carboxyfluorescein, 5-carboxyrhodamine, 6-carboxyrhodamine, 6-carboxytetramethyl amino phthalocyanine, azomethine, cyanine (Cy3, Cy3.5, and Cy5), xanthine, succinylfluorescein, aminoacrydine, quantum dots, carbon allotropes, cyanide, thiols, chlorine, bromine, methyl, phosphorous, sulfur, etc., but the Raman-active material is not limited thereto, and the Raman-active material used should show a distinct Raman spectrum. Preferably, the Raman-active material may be cyanine-based organic fluorescent molecules (Cy3, Cy3.5, and Cy5); organic fluorescent molecules including FAM-, Dabcyl-, Rhodamine-based fluorescent molecules; or non-fluorescent Raman-active materials including mercaptobenzoic acid and aminothiophenol, but the Raman-active material is not limited thereto. These organic fluorescent molecules have an advantage in that they can detect a higher Raman signal by resonating with the excitation laser wavelength used in Raman analysis, but the scope of the present invention is not limited thereto.

For example, in the preparation method of the present invention, the shape of the core made of the first metal determines the shape of the core-gap-shell nanoparticles to be finally formed. Further, it may affect the optical properties of the core-gap-shell nanoparticles to be finally formed. The core made of the first metal may be spherical, rod-shaped, cube-shaped, or prismatic particles, but the shape of the core made of the first metal is not limited thereto.

Another aspect of the present invention provides a core-gap-shell nanoparticle showing a surface-enhanced Raman scattering (SERS) signal and having a hollow space between a core and a shell, in which a Raman-active material with an average height of a few nanometers is disposed. Specifically, the core-gap-shell nanoparticle of the present invention includes a gap, which is a hollow space formed between a core and a shell, by selectively removing all or part of a second metal from the core made of a first metal and a shell made of an alloy of the second metal and a third metal; wherein, in the shell made of the alloy of the second metal and the third metal, the content of the second metal with respect to that of the third metal decreases progressively from the surface of the first metal core outward; and wherein the finally formed core-gap-shell nanoparticle maintains the gap through one or more metal bridges, which connect the core and the shell, comprising the second metal, the third metal, or both thereof.

For example, the core-gap-shell nanoparticle of the present invention may be a nanoparticle, a surface of which is bound to a nucleic acid, polypeptide, or ligand that specifically interacts with a subject to be detected or imaged, for subsequent application in biosensing and/or bioimaging.

The nanoparticle of the present invention may be prepared according to the method for preparing the core-gap-shell nanoparticle of the present invention described above.

Still another aspect of the present invention provides a composition for biosensing or bioimaging, which comprises the core-gap-shell nanoparticle described above.

As described above, the core-gap-shell nanoparticle of the present invention can be detected by SERS, and thus it can be utilized for biosensing and bioimaging through SERS.

In particular, the core-gap-shell nanoparticle to be used may be a nanoparticle, a surface of which is bound to a nucleic acid, polypeptide, or ligand that specifically interacts with a subject to be detected or imaged. For example, for detection of specific DNA, the presence of target DNA can be confirmed by: allowing a DNA fragment, which includes a sequence complementary to part of the target DNA to be detected, to bind to a surface of the core-gap-shell nanoparticle; allowing the resultant to come into contact with a sample, which is expected to include the target DNA, along with magnetic beads, which are labeled with a DNA fragment including a sequence complementary to other part(s) of the target DNA; recovering the magnetic beads using a magnet; and measuring a Raman signal from the Raman-active material contained in the core-gap-shell nanoparticle of the present invention to determine whether the signal is generated; and furthermore, the signal intensity can be measured and quantified. Alternatively, the desired cells may be imaged using nanoparticles, in which a protein or polypeptide that can selectively bind to proteins specifically expressed in cells to be imaged is bound to a surface of the core-gap-shell nanoparticle; followed by the measurement of Raman signals.

In a specific embodiment of the present invention, it was confirmed that a hepatitis A virus gene (i.e., target DNA) can be detected with a low detection limit of 10 aM to 100 aM using core-gap-shell nanoparticles that are labeled with DNA complementary to part of the hepatitis A virus DNA. In addition, strong SERS signals were observed in integrin $\alpha_v\beta_3$-positive U87MG cells using core-gap-shell nanoparticles labeled with a cyclo(Arg-Gly-Asp-D-Phe-Lys) (c(RGDyK); hereinafter denoted as "cRGD") peptide, which specifically binds to $\alpha_v\beta_3$ integrin that is overexpressed in metastatic and endothelial tumor cells; however, the SERS signals were not observed in $\alpha v\beta 3$-negative MCF-7 cells, thus confirming that bioimaging is possible with high selectivity.

For example, the composition according to the present invention for biosensing or bioimaging may be provided along with a buffer solution so as to provide an environment suitable for DNA hybridization and/or a binding with proteins, polypeptides, ligands, receptors, etc., but the composition is not limited thereto. In particular, the buffer solution may be a phosphate buffer (e.g., PBS, PBSS, etc.) widely used in the art, but the buffer solution is not limited thereto.

DETAILED DESCRIPTION OF THE INVENTION

Hereinafter, the present invention will be described in more detail with reference to the following Examples. However, these Examples are for illustrative purposes only, and the scope of the invention is not limited by these Examples.

Reagents and Materials

Gold nanoparticles (AuNPs, average diameter of 40 nm) and magnetic microparticles (MMPs, Dynabeads® MyOne™ carboxylic acid, average diameter of 1 µm) were purchased from Ted Pella, Inc. (Redding, CA, USA) and Invitrogen Dynal AS (Oslo, Norway), respectively. HPLC-purified oligonucleotides were purchased from Bioneer (Daejeon, Korea), and carboxymethyl-PEG-thiol (CM-PEG-SH, Mw: about 5,000) was purchased from Laysan Bio, Inc. (Arab, AL, USA). Cyclo(Arg-Gly-Asp-D-Phe-Lys) (c(RGDyK), cRGD) peptides were purchased from Peptides International, Inc. (Louisville, KY, USA). Gold(III) chloride trihydrate ($HAuCl_4 \cdot 3H_2O$, ≥99.9%), silver nitrate ($AgNO_3$, 99.9999%), 4-mercaptopyridine (4-MPy, 95%), polyvinylpyrrolidone (PVP, Mw: about 40,000), ammonium hydroxide solution ($NH_4OH$, 28.0% to 30.0% $NH_3$ basis), L-ascorbic acid (AA, ≥99.0%), iron(III) nitrate nonahydrate ($Fe(NO_3)_3 \cdot 9H_2O$, ≥98.0%), 2-(N-morpholino)ethanesulfonic acid (MES, ≥99.0%), N-(3-dimethylaminopropyl)-N'-ethylcarbodiimide hydrochloride (EDC, commercial grade), N-hydroxysulfosuccinimide sodium salt (Sulfo-NHS, ≥98%), ethylenediaminetetraacetic acid (EDTA, 99.4% to 100.06%), DL-dithiothreitol (DTT, ≥99.0%), Tween®-20, and sodium dodecyl sulfate (SDS, ≥98.5%) were all purchased from Sigma-Aldrich (St. Louis, MO, USA). Tris [hydroxymethyl]aminomethane (Tris, 99.8% to 100.1%) was purchased from USB Corporation (Cleveland, OH, USA). Ethyl alcohol (anhydrous, 99.9%) and sodium chloride (NaCl, ≥99.0%) were purchased from DAEJUNG Chemicals & Metals Co. (Siheung, Gyeonggi, Korea). All of the chemical reagents were used as received without further purification. NANOpure water (Millipore, Milli-Q 18.2 MΩ·cm) was used throughout the experiments.

PREPARATION EXAMPLE 1

Preparation of 4-MPy-Modified Au Nanoparticles

To attach the Raman reporter molecules (4-mercaptopyridine, 4-MPy) onto the AuNPs, 10 µL of an ethanol solution of 4-MPy (1 mM) was injected into 1 mL of a solution (100 pM) of the AuNPs (average diameter of 40 nm). The resulting mixture was shaken for 2 hours. Then, the 4-MPy-modified AuNPs formed (MPy-AuNPs) were washed with distilled water by centrifugation at 6,000 rpm for 10 minutes and redispersed in distilled water for further use.

PREPARATION EXAMPLE 2

Synthesis of Au/Au—Ag Core/Alloy Shell Nanoparticles

The Au/Au—Ag core/alloy shell NPs (CAS NPs) were synthesized using a known procedure with minor modifications (*Nanoscale*, 2016, 8: 11707-11717). Specifically, 200 µL of the MPy-AuNPs solution (100 pM) and 200 µL of a polyvinylpyrrolidone (PVP, Mw: about 40,000) solution (1 wt %) were mixed gently. Then, 50 µL of a $AgNO_3$ solution (1 mM), 16 µL of a solution of $NH_4OH$, and 150 µL of a solution of $HAuCl_4$ (1 mM) were sequentially added to the mixture. Then, 200 µL of an L-ascorbic acid (AA) solution (20 mM) was immediately injected into the mixture with gentle shaking. The mixture finally obtained was shaken gently at room temperature for 1 hour. Finally, the solution was washed twice with distilled water by centrifugation at 6,000 rpm for 10 minutes, and then redispersed in distilled water.

COMPARATIVE EXAMPLE 1

Synthesis of Gapless Au/Au Core/Shell Nanoparticles

The synthesis of the gapless Au/Au core/shell NPs (gapless AuNPs) was performed by modifying the method for synthesis of the CAS NPs in Preparation Example 2. Specifically, 200 μL of the $HAuCl_4$ solution (1 mM) was added instead of 50 μL of the $AgNO_3$ (1 mM) solution and 150 μL of the $HAuCl_4$ solution (1 mM) during the synthesis process. The rest of the procedure was the same as that for the synthesis of the CAS NPs in Preparation Example 2.

EXAMPLE 1

Synthesis of Au—Ag Dealloyed Intra-Nanogap Particles

The Au—Ag dealloyed intra-nanogap particles (DIPs) were synthesized by injecting $Fe(NO_3)_3$ as a Ag etchant into the CAS NPs prepared according to Preparation Example 2. Specifically, 100 μL of a solution of the CAS NPs (100 pM) was mixed with 100 μL of a PVP solution (1 wt %). Then, 125 μL of an $Fe(NO_3)_3$ solution (20 mM) was injected into the mixture with gentle shaking. The resulting mixture was shaken mildly at room temperature for 30 minutes, washed twice with distilled water by centrifugation at 6,000 rpm for 10 minutes, and redispersed in distilled water.

EXPERIMENTAL EXAMPLE 1

Micro-Raman Spectroscopy

For the solution-state Raman analysis, a solution of the as-synthesized NPs (100 pM) was loaded into a capillary tube (soda lime glass; Cat. No. 2502, Kimble Chase, Vineland, NJ, USA). All Raman measurements were performed using a Renishaw inVia microscope equipped with 514 nm (5 mW), 633 nm (4 mW), and 785 nm (4 mW) excitation lasers, a 20×objective lens (NA=0.40, Leica), and a standard charge-coupled device (CCD) array detector (576×384 pixels; Peltier; cooled to −70° C.). The surface-enhanced Raman scattering (SERS) spectra were obtained using an acquisition period of 10 seconds and were recorded for wavenumbers of 800 $cm^{-1}$ to 1,800 $cm^{-1}$.

EXPERIMENTAL EXAMPLE 2

AFM-Correlated Raman Spectroscopy

To obtain the SERS spectra from the individual NPs, an AFM-correlated Raman microscope (Ntegra, NT-MDT) equipped with an inverted optical microscope (IX 73, Olympus) was employed. The AFM-based multistep tip-matching procedure was performed based on previous studies in order to accurately match the end of the AFM tip and the laser focal spot. First, the laser beam was focused on the upper surface of a particle-loaded cover glass slip (poly-L-lysine-coated cover glass), and the end of the AFM tip was positioned at the laser focal spot, which was observed with micrometer-level accuracy using a video camera. Then, Rayleigh scattering images were recorded while scanning the tip along the x- and y-axes, and the AFM tip was subsequently moved to the region with the highest scattering intensity such that the tip was located at the laser focal spot. Finally, the end of the AFM tip was moved with nanometer-level precision while observing the intensity of the Raman signal of the silicon (520 $cm^{-1}$) in the AFM tip. The highest Raman signal intensity was obtained when the end of the AFM tip was located exactly at the center of the laser focal spot. In this tip-matching state, Rayleigh scattering images and AFM topographical images were obtained simultaneously using a piezoelectric x, y sample scanner. The SERS spectra of the individual NPs were obtained using a CCD detector (1,024×256 pixels; Peltier; cooled to −70° C., Andor) and a 633 nm excitation laser (a He—Ne laser, Thorlabs). The exposure time was 20 seconds, and the laser power was 60 μW. An oil-immersed microscope objective (100×, NA=1.4, Olympus) was used to focus the laser beam on a diffraction-limited spot (about 250 nm when a 633 nm laser was used).

EXPERIMENTAL EXAMPLE 3

Theoretical Calculations

Figure 1:
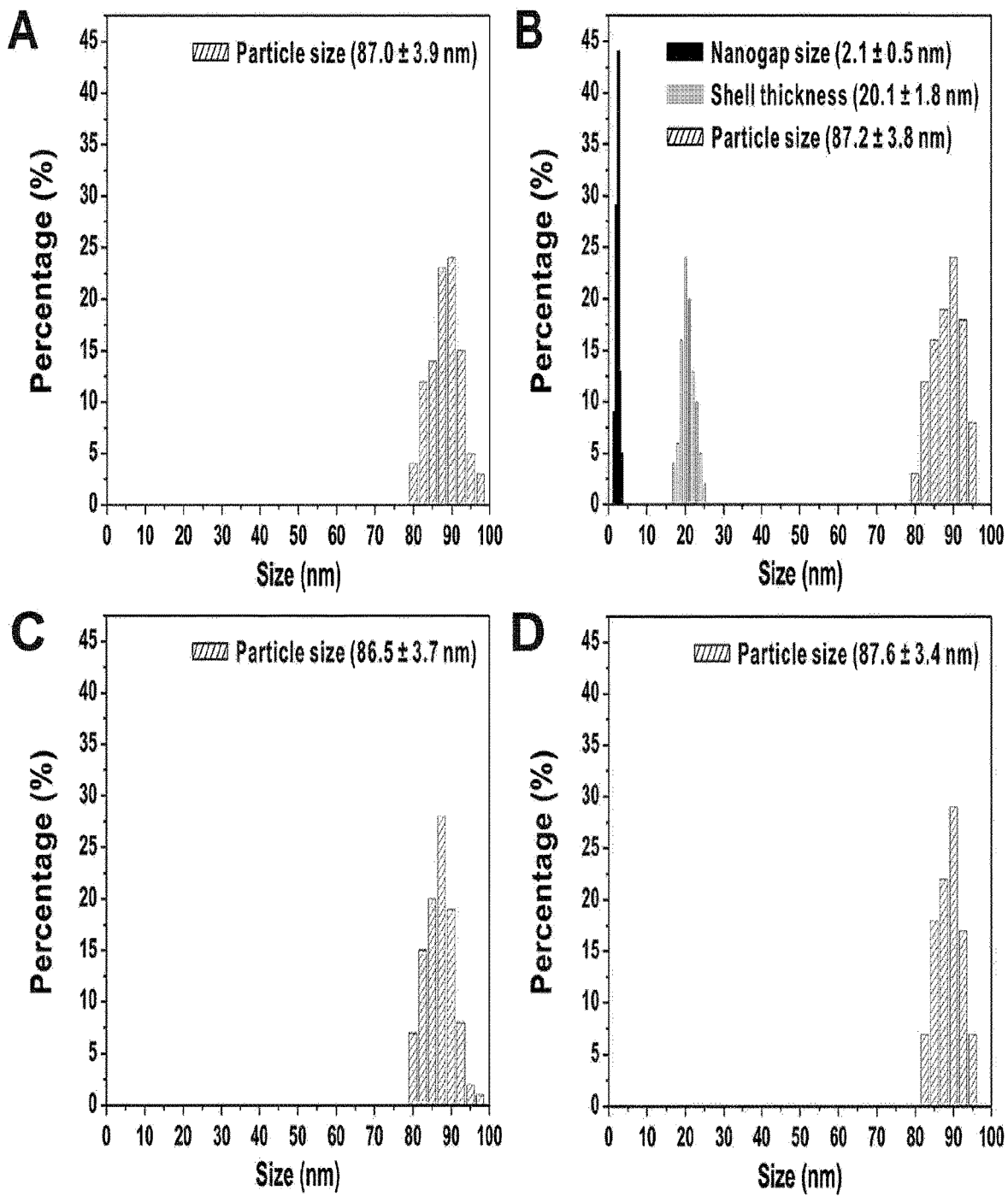
FIG. 1 shows graphs illustrating the intra-nanogap (i.e., interior nanogap), shell thickness, and particle size distributions of the as-synthesized nanoparticles (NP), in which In FIG. 1, A represents CAS NPs, B represents DIPs, C represents gapless AuNPs before Ag etching, and D represents gapless AuNPs after Ag etching. The data were obtained from high-resolution TEM (HR-TEM) images of 100 individual particles.

The extinction spectra of the NPs were calculated using the Mie theory. An analytic model was used for the dielectric functions of Au and an Au—Ag alloy. The particles were considered as being embedded in water (ε=1.332). The average particle sizes, intra-nanogap sizes, shell thicknesses, and atomic compositions of the as-synthesized NPs are shown in FIG. 1 and Table 1. The Smith method for effective dielectric function of the intra-nanogap region of DIPs was used, and the intra-nanogap region was modeled as a mixture of gold and water. For metal-rich mixtures, an average unit within the intra-nanogap was considered as a spherical dielectric inclusion surrounded by the spherical shell of the metal. The effective dielectric function is a value that does not alter the electric field under replacement of the unit structure with a homogeneous effective medium. This model mostly targets metal-rich mixtures but is also applicable to dielectric-rich mixtures whose metallic parts are connected to each other and whose overall behavior is thus conductive. The structure of the present invention is such that the mixture within the intra-nanogap is in the form of a thin shell and is squeezed between a metallic core and a shell, and each inclusion can be conductive.

TABLE 1

| | Au (atomic %)[†] | Ag (atomic %)[†] |
|---|---|---|
| Amount of metal precursor added during synthesis[‡] | 75.0 | 25.0 |
| CAS NPs | 77.2 | 22.8 |
| DIPs | 91.4 | 8.6 |
| Gapless AuNPs | 100 | 0 |

[†]Atomic composition was estimated by EDX elemental mapping.
[‡]Different volumes of metal precursors (Au = 150 μL, Ag = 50 μL) were used for synthesis of an alloy shell.

EXPERIMENTAL EXAMPLE 4

Calculations of SERS Enhancement Factor

Figure 2:
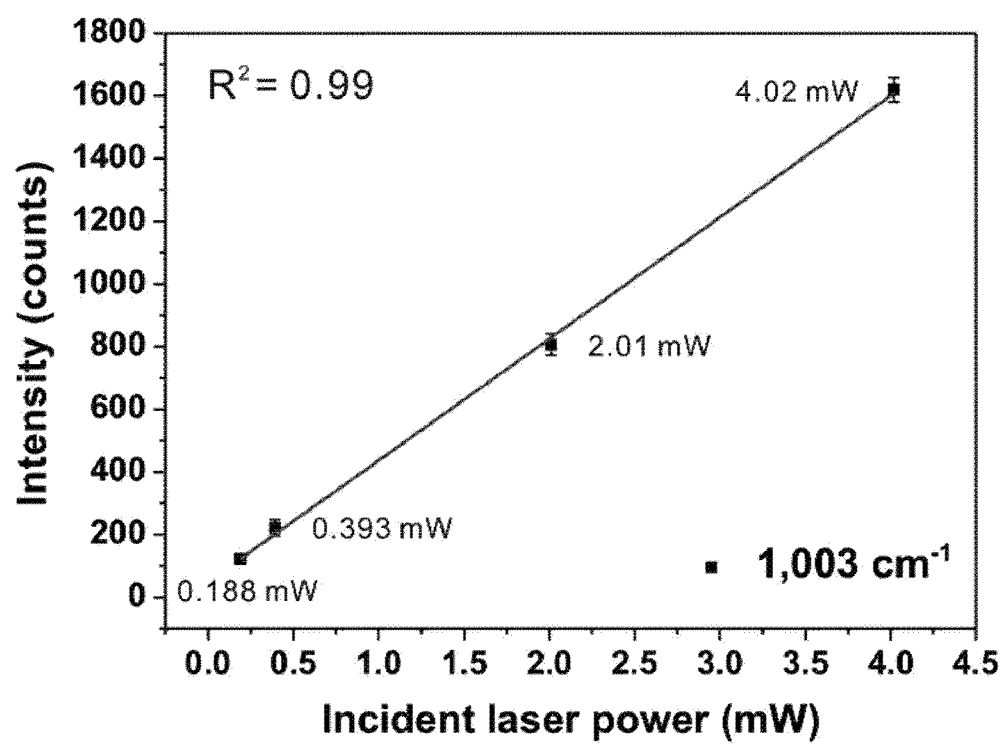
FIG. 2 shows a graph illustrating the incident laser power-dependent Raman intensity of a 4-MPy solution. The Raman intensity of the fingerprint peak at 1,003 $cm^{-1}$ was plotted as a function of the incident laser power. All of the Raman spectra were obtained using a 633 nm laser through an objective lens (20×, NA=0.4) with an exposure time of 30 seconds. The 4-MPy solution was used at the same concentration (200 mM) for all of the experiments.

The SERS enhancement factor (EF) can be calculated using the following Equation 1:

$$\text{Enhancement factor}(EF) = \frac{I_{SERS}}{N_{SERS}} \Big/ \frac{I_{BULK}}{N_{BULK}} \quad (1)$$

where $I_{SERS}$ and $I_{BULK}$ are the intensities of the Raman peak at 1,003 cm$^{-1}$ for the individual DIP and the pure 4-MPy solution (200 mM, 22.23 mg/mL), respectively; and $N_{SERS}$ and $N_{BULK}$ are the number of 4-MPy molecules on a single DIP and within the solution, respectively. The number of 4-MPy molecules on a single DIP ($N_{SERS}$) was estimated by assuming that the maximum number of 4-MPy molecules (with a monomolecular area of about 0.18 nm$^2$) were packed on the AuNPs (average diameter of 40 nm). To estimate $I_{BULK}$ and $N_{BULK}$, 12 µL of a 4-MPy solution (200 mM, 22.23 mg/mL) was introduced into a sticker chamber placed on a glass substrate and illuminated with a 633 nm laser for 30 seconds through an objective lens (20×, NA=0.4). Assuming that the effective excitation volume ($V_{BULK}$) was a cylinder, the height (h) was calculated using the following Equation 2:

$$\frac{h}{2r} = \frac{3.28\eta}{NA} \quad (2)$$

where η is the refractive index of the medium (water; 1.33) and r is the radius of the laser beam (5 µm). Further, $N_{BULK}$ can be calculated using the following Equation 3:

$$N_{BULK} = (V_{BULK} \times D/M) \times N_A \quad (3)$$

where D is the density of 4-MPy (22.23 mg/mL), M is the molar mass of 4-MPy (111.16 g/mol), and $N_A$ is Avogadro's constant (6.02×10$^{23}$ mol$^{-1}$). Finally, the incident laser power-dependent Raman intensities of the 4-MPy solution were measured and plotted to determine the value of $I_{BULK}$ for calculating the SERS EF (FIG. 2).

EXPERIMENTAL EXAMPLE 5

Preparation of DNA-Modified Magnetic Microparticle

DNA-modified magnetic microparticles (DNA-MMPs) were prepared according to the manufacturer's instructions (Invitrogen Dynal AS) with minor modifications. Specifically, 200 µL of a solution of the MMPs coated with the carboxyl functional group (10 mg/mL) was transferred to a tube and placed in a magnetic separator to remove the supernatant. After the supernatant had been discarded, the MMPs were washed twice with 200 µL of 100 mM MES buffer (pH 4.8) and redispersed in 20 µL of the MES buffer. Then, 10 µL of 5'-amine-modified oligonucleotides (1 mM, SEQ ID NO. 1: 5'-NH$_2$-A$_{10}$-PEG$_6$-AGAAAGAGGAGT-TAA-3') and 10 µL of a 1 M EDC solution in MES buffer (100 mM, pH 4.8) were added to the washed MMPs, and the resulting mixture was stirred at room temperature for 4 hours. Finally, the mixture was washed three times with 200 µL of a washing buffer (250 mM, Tris pH 8.0, 0.01% Tween®-20), and the DNA-modified MMPs were suspended in 200 µL of a storage buffer (10 mM, Tris pH 8.0, 1 mM EDTA).

EXPERIMENTAL EXAMPLE 6

Preparation of DNA-Modified DIP Raman Probes

To prepare the DNA-modified DIP Raman probes (DIP probes), thiolated oligonucleotides were attached onto the DIPs through a Au—S binding. First, disulfide-modified oligonucleotides were reduced in a 100 mM DTT solution at room temperature for 2 hours and purified using an NAP-5 column (Sephadex™ G-25 DNA Grade, GE Healthcare, UK) to obtain thiolated oligonucleotides. Then, the freshly DTT-reduced thiolated oligonucleotides (SEQ ID NO. 2: 5'-TCCATGCAACTCTAA-A$_{10}$-SH-3') were added to a solution of the 6 DIPs and allowed to incubate overnight at room temperature with mild shaking. The solution was then adjusted to obtain a final phosphate concentration of 10 mM (pH 7.4) and an SDS concentration of 0.1% (wt/vol). After incubating for 1 hour, the mixture was adjusted to 0.3 M NaCl by the gradual addition of six aliquots of a 2 M NaCl solution at intervals of 1 hour. Then, the mixture was maintained at room temperature overnight with mild shaking, and thereafter the mixture was washed three times with an assay buffer (10 mM phosphate buffer, 0.3 M NaCl, 0.01% SDS, pH 7.4) by centrifugation at 6,000 rpm for 5 minutes and redispersed in the assay buffer for use as a DNA detection assay.

EXPERIMENTAL EXAMPLE 7

SERS-Based DNA Detection Assay

SERS-based DNA detection assays were performed using a conventional sandwich-hybridization assay. First, a solution of the target DNA (hepatitis A virus; HAV, SEQ ID NO. 3: 5'-TTAGAGTTGCATGGATTAACTCCTCTTTCT-3') was serially diluted from a concentration of 10 aM to 1 pM using an assay buffer (10 mM phosphate buffer, 0.3 M NaCl, 0.01% SDS, pH 7.4). In addition, non-complementary DNA (hepatitis B virus; HBV, SEQ ID NO. 4: 5'-TTGGCTTTCAGTTATATGGATGATGTGGTA-3') was also used so as to confirm the DNA targeting specificity of the probes. Then, 100 µL of the diluted target DNA solution was mixed with 1 µL of the DNA-MMP solution (10 mg/mL), and the mixture was allowed to incubate at room temperature with shaking for 1 hour. Then, 20 µL of the DIP probe solution (100 pM) was added to the target DNA-capturing MMP solution, and the mixture was allowed to incubate at room temperature with shaking for 30 minutes. The target-captured DIP probe-MMP complexes were washed three times with an assay buffer and the final solution volume was adjusted to 10 µL. For the Raman measurements, 5 µL of the concentrated solution was transferred onto a cover glass placed on a magnet. Due to the magnetic force applied, the complexes were collected on the surface of the cover glass. The remaining solvent was wiped out with tissue paper, and the collected complexes were dried under ambient conditions and used for the Raman measurements. To reduce the variance in the unevenness of the focal spot of the prepared sample, the dried cover glass was flipped over, and the focus was adjusted on the backside of the sample. All of the Raman measurements were performed using a Renishaw inVia microscope equipped with a 785 nm excitation laser (2 mW). The SERS spectra were obtained using an acquisition time of 5 seconds. For clear identification, the SERS intensities were obtained by consecutive accumulation of five measurements.

EXPERIMENTAL EXAMPLE 8

Preparation of cRGD Peptide-Modified DIP Imaging Probes

To perform SERS-based target-specific cell imaging, the surfaces of the DIPs were functionalized with a cRGD peptide, which has a high affinity for integrin $\alpha_v\beta_3$. To prepare PEGlyated DIPs, first, 50 µL of a 0.5 mM solution of CM-PEG-SH (Mw: about 5,000) was added to 500 µL of a dispersion solution of the DIPs (50 pM) prepared in 0.01% SDS, and the mixture was allowed to stand overnight at room temperature with mild shaking. The mixture was washed twice with a 50 mM MES buffer solution (pH 4.8) by centrifugation at 6,000 rpm for 5 minutes. Then, the carboxylic acid part of the PEG attached onto the DIPs was linked with the cRGD peptide through an EDC/Sulfo-NHS coupling reaction. Specifically, 25 µL of freshly prepared 20 mM EDC and Sulfo-NHS solutions were sequentially added to 500 µL of the freshly prepared PEGlyated DIPs (25 pM), and the reaction mixture was stirred for 20 minutes. The thus-obtained mixture was washed twice with a 10 mM phosphate buffer (pH 7.4) by centrifugation at 6,000 rpm for 5 minutes, and the supernatant was discarded. To this concentrated solution was added 125 µL of the cRGD peptide (1 mM) dissolved in a 10 mM phosphate buffer (pH 7.4), and the reaction mixture was shaken for 6 hours. Then, it was washed twice with a 10 mM phosphate buffer (pH 7.4) by centrifugation at 6,000 rpm for 5 minutes and dispersed in phosphate buffered saline (10 mM phosphate buffer, 0.15 M NaCl, pH 7.4) for further use.

EXPERIMENTAL EXAMPLE 9

SERS-Based Target-Specific Cell Imaging

The human malignant U87MG glioma cell line and the human breast carcinoma MCF-7 cell line were obtained from the American Type Culture Collection (ATCC) and were cultured in Minimum Essential Medium (MEM) and Dulbecco's Modified Eagle Medium (DMEM) along with 10% fetal bovine serum (FBS), penicillin (100 U/mL), and streptomycin (100 µg/mL) at 37° C. under 5% $CO_2$. Both types of cells were detached with trypsin and dispensed ($5\times10^3$ cells/mL) into poly-D-lysine-coated 50 mm glass-bottom dishes (MatTek Corporation, Ashland, MA, USA) and incubated overnight. Thereafter, the dishes in which the cells were cultured were washed with PBS buffer (10 mM phosphate buffer, 0.15 M NaCl, pH 7.4), filled with the cRGD-functionalized DIPs dispersed in a medium (12.5 pM), and maintained at 37° C. under 5% $CO_2$ for 6 hours. After incubation, the cell monolayer was washed with PBS buffer and fixed with 4% paraformaldehyde. To perform SERS-based target-specific cell imaging, the cells incubated with the cRGD-functionalized DIPs were scanned, and the SERS spectrum at each mapping pixel (2 µm×2 µm) was recorded. All of the Raman measurements were performed using a Renishaw inVia microscope system equipped with a 785 nm (4 mW) or 633 nm (400 µW) excitation laser, and the SERS signals were recorded for an acquisition time of one second for each mapping pixel. Finally, the integrated SERS intensities (from 983 $cm^{-1}$ to 1,023 $cm^{-1}$) for each mapping pixel were color-scaled for cell imaging.

EXPERIMENTAL EXAMPLE 10

Characteristic Analysis

The morphological characteristics of the as-synthesized NPs and the target DNA-induced sandwich hybridization complexes were evaluated using a TEM system (JEM-2100, JEOL), a high-resolution TEM (HR-TEM) system (JEM-2100F, JEOL), and a field-emission SEM (FE-SEM) system (JSM-7800F Prime, JEOL). In addition, the elemental maps and line scan profiles of the NPs were obtained using an EDX system (INCA, Oxford Instruments) coupled with an HR-TEM system. In addition, the UV-Vis spectra were obtained using a UV-Vis spectrophotometer (HP 8453, Agilent Technologies).

Results

Figure 3:
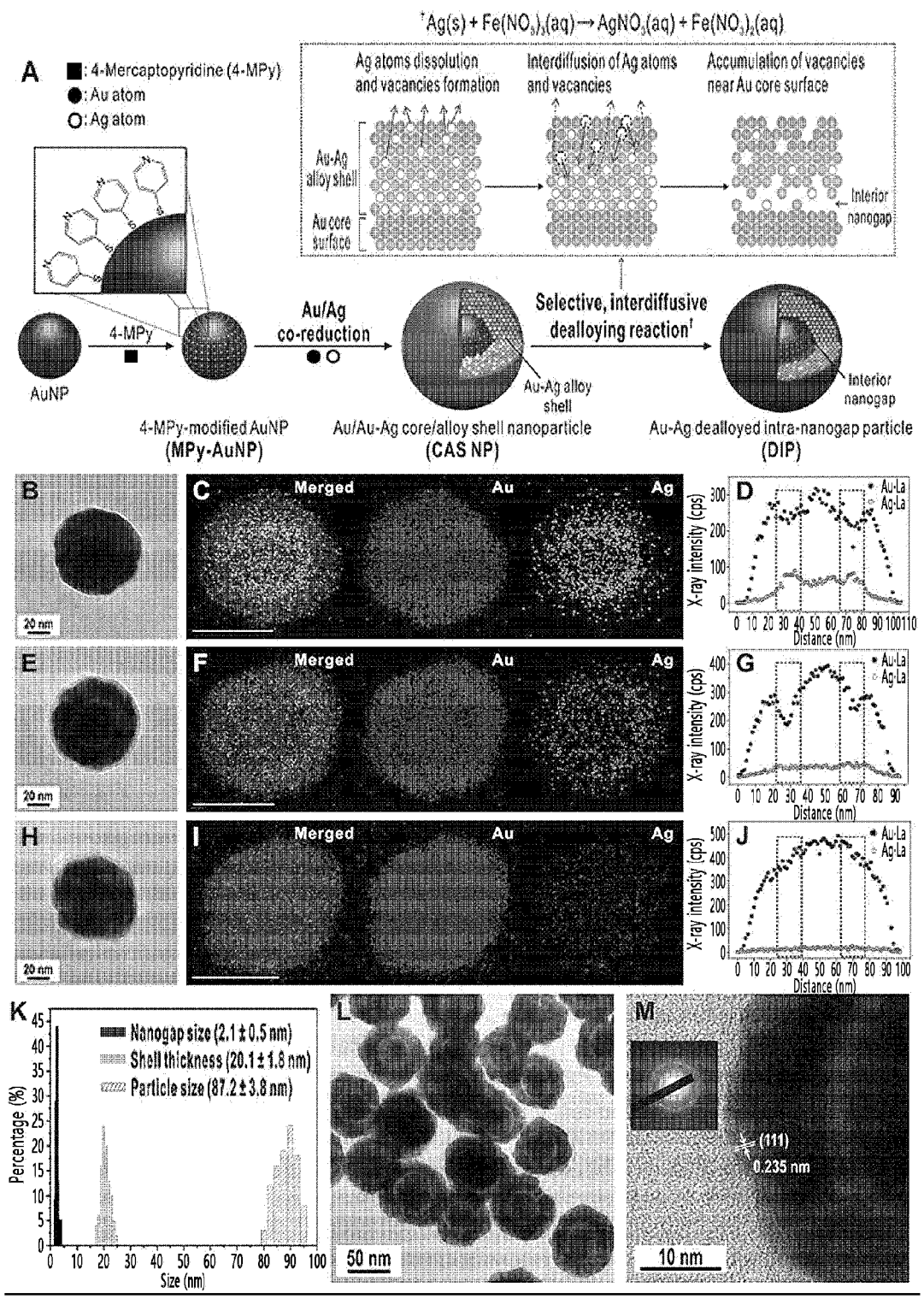
FIG. 3 shows drawings illustrating a synthetic strategy and characteristics of dealloyed intra-nanogap particles.
Figure 5:
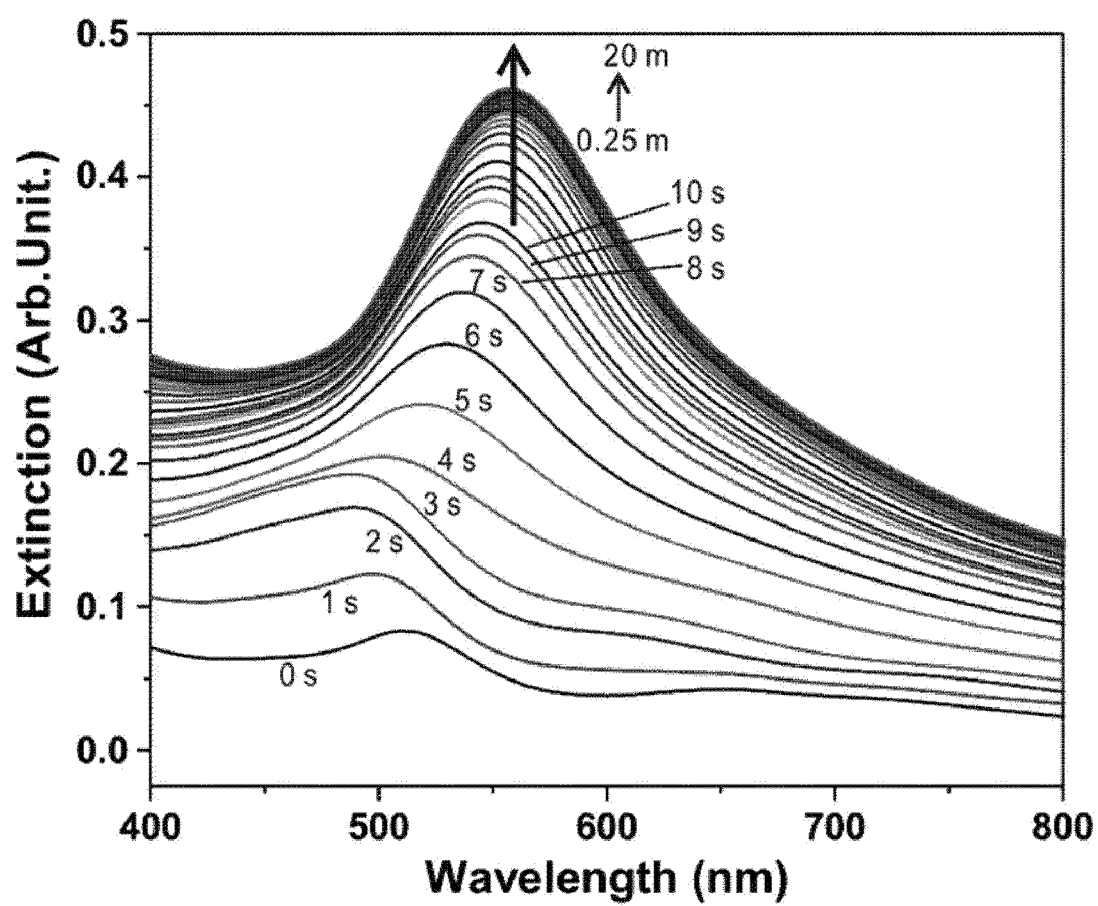
FIG. 5 shows a graph illustrating the change in UV-Vis spectrum of a CAS NP reaction mixture during the process of alloy shell formation.
Figure 6:
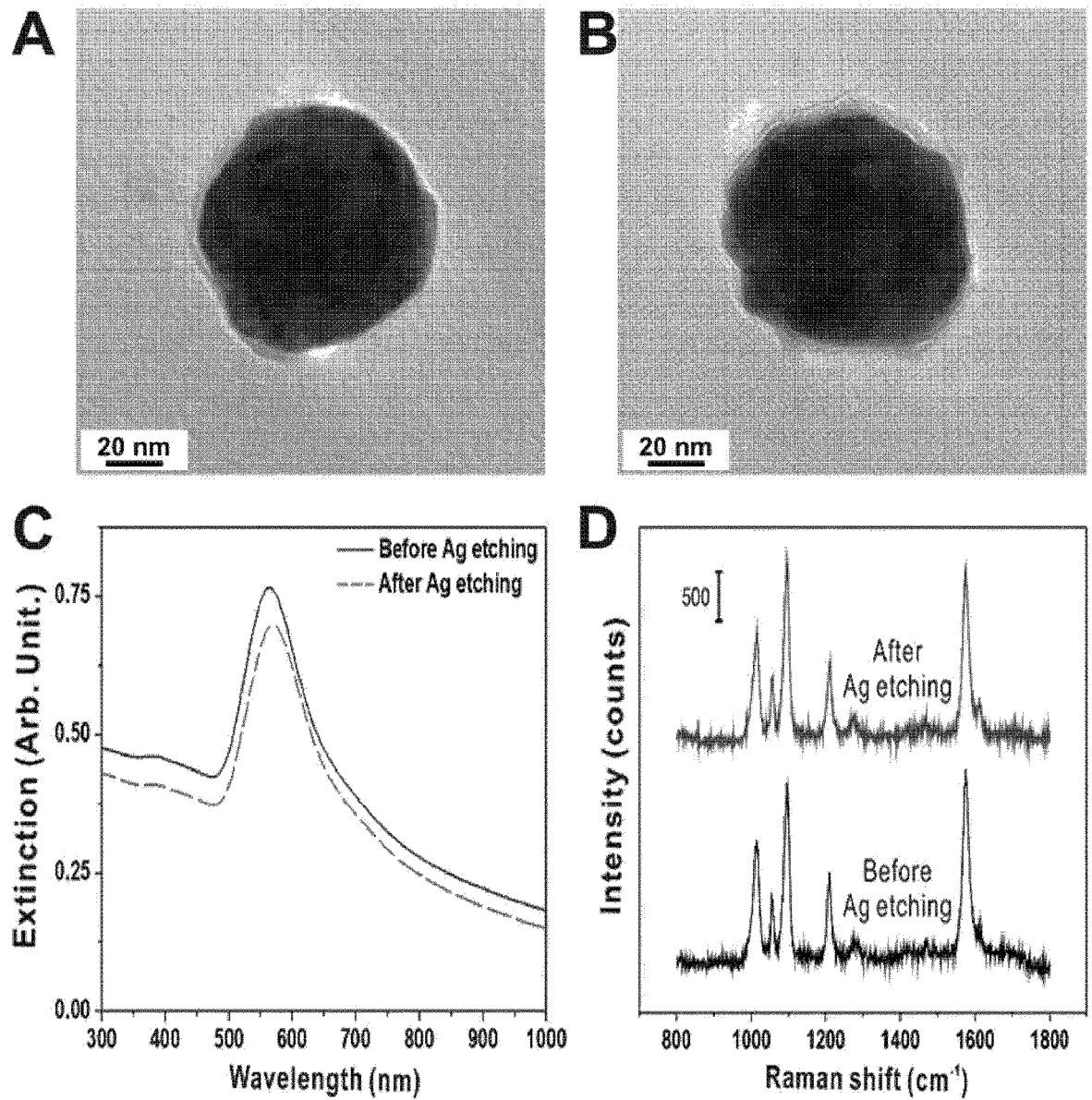
FIG. 6 shows drawings illustrating the structural changes and optical properties of gapless AuNPs during a Ag etching reaction, in which, in FIG. 6, A and B show the TEM images of gapless AuNPs before and after the Ag etching, respectively; C shows the UV-Vis spectra of the gapless AuNPs before and after the Ag etching reaction; and D shows a solution-based SERS spectrum of gapless AuNPs before and after the Ag etching reaction. All of the spectra were obtained using a 633 nm laser (4 mW laser power) with an exposure time of 10 seconds using the same particle concentration (100 pM). The morphology, UV-Vis spectra, and SERS spectra were shown to be similar regardless of performance of the Ag etching reaction, indicating that the ferric nitrate-based dealloying reaction is a Ag-specific/selective dissolution reaction.

Selective-Interdiffusive Dealloying-Based Synthesis of Nanoparticles with an Interlayer-Free Intra-Nanogap To synthesize the DIPs using the SID process, Au/Au—Ag core/alloy shell nanoparticles (CAS NPs) were formed through a co-reduction process involving the simultaneous reduction of $HAuCl_4$ and $AgNO_3$ on 4-MPy-modified AuNPs (MPy-AuNPs) (FIG. 3, B). The average size of the CAS NPs, as measured from transmission electron microscopy (TEM) images, was about 87.0 nm (FIG. 1), while the atomic composition of the shell region was estimated to be $Au_{77.2}Ag_{22.8}$ (Table 1). Interestingly, the reduced Au and Ag atoms were not evenly distributed throughout the entire shell region (FIG. 3, C and Table 4A). An energy-dispersive X-ray spectroscopy (EDX) line scan performed across the centers of the CAS NPs showed that most of the Ag atoms were located near the Au core, with the number of Au atoms decreasing near the Au core (FIG. 3, D--dotted box). In general, a higher standard reduction potential of the Au precursor results in faster reduction compared to the case for the Ag precursor ($AuCl_4^-/Au=0.99$ V and $Ag^+/Ag=0.8$ V versus standard hydrogen electrode). The strong affinity between Ag and the pyrrolidone groups of polyvinylpyrrolidone (PVP) increases the reduction rate of the Ag precursor in the early stages, which results in the accumulation of Ag atoms at a faster rate near the Au core. To more specifically confirm this phenomenon, the changes in the extinction peak of the CAS NPs during the alloy shell formation process were monitored (FIG. 5). In the early stages of the alloy shell formation process, the extinction peak exhibited a rapid blue shift, suggesting the formation of Ag layers. Then, as the reaction progressed, the extinction peak underwent a gradual red-shift to a long wavelength, with the intensity of the peak increasing. This indicates the formation of larger CAS NPs.

Figure 4:
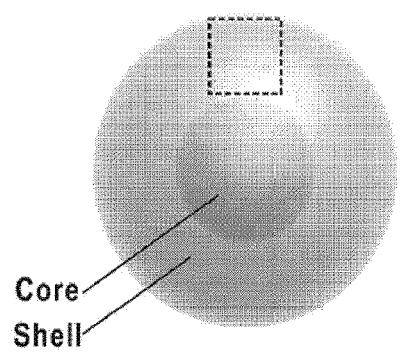
FIG. 4 shows drawings illustrating the EDX elemental maps of as-synthesized NPs, in which, in FIG. 4, A represents the EDX elemental map of CAS NP, B represents the EDX elemental map of DIP, and C represents the EDX elemental map of gapless AuNPs. These maps show elemental distributions of Au and Ag in the shell region (the dotted box in the left figure). The scale bar is 10 nm.
Figure 4:
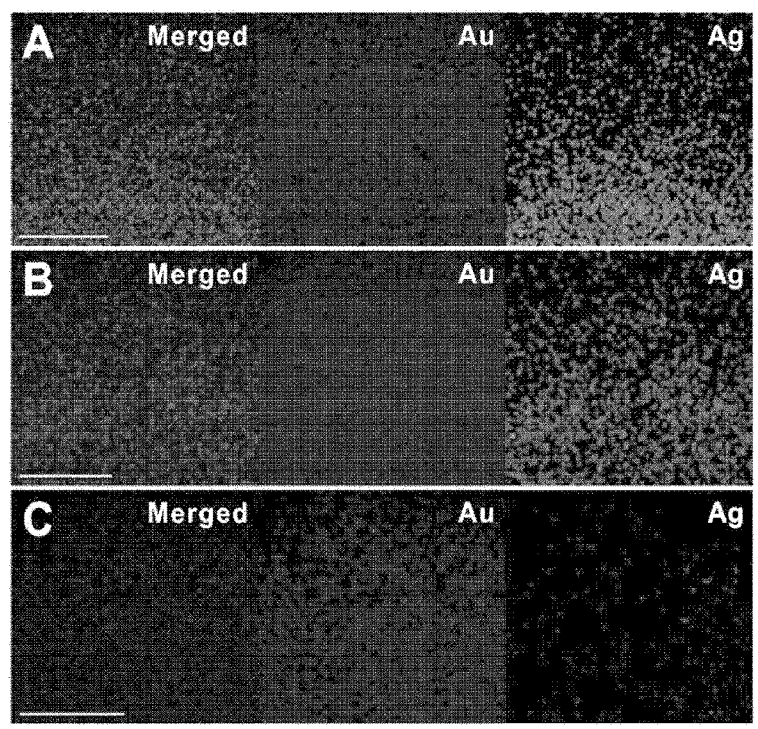

Next, ferric nitrate ($Fe(NO_3)_3$) was introduced into the CAS NPs to selectively dissolve the Ag atoms (FIG. 3, A). As can be seen in FIG. 3E, it was confirmed that the Ag-etched CAS NPs have a nanogap present between the core and the shell due to the dealloying process. The average size of the DIPs (about 87.2 nm) was similar to that of the CAS NPs, with the intra-nanogap and the shell size of the DIPs being about 2.1 nm and about 20.1 nm, respectively (FIG. 3, K). The EDX elemental maps of the DIPs confirm that the Ag atoms near the Au core were almost completely etched away (FIG. 3, F and FIG. 4, B), and the EDX line scan profile indicates that the number of Ag atoms near the Au core rapidly decreased after the dealloying reaction (FIG. 3, G--dotted box); the proportion of Ag atoms in the shell region was lower compared to that in the CAS NPs (Table 1). Further, the Au-Lα curve for the area near the Au core was shown to be valley-shaped when the Ag-Lα peak disappeared (FIG. 3, G--dotted box), confirming that the intra-nanogap is formed by the selective removal of the Ag atoms near the Au core. In contrast to the case for the DIPs, the intra-nanogap was not observed in the case of the gapless Au/Au core/shell NPs (gapless AuNPs), whose shell was composed only of Au and not a Au—Ag alloy (FIG. 3, H). The average size of the gapless AuNPs was also similar to that of the CAS NPs (FIG. 1), with the shell being composed entirely of Au atoms (FIG. 3, I, FIG. 4, C, and Table 1). In addition, a valley-like Au-Lα plot was not observed (FIG. 3, J--dotted box), confirming that the NPs had a nanogapless structure. When $Fe(NO_3)_3$ was introduced into the as-synthesized gapless AuNPs, there was no change in the morphology or the ultraviolet-visible (UV-Vis) and SERS spectra of the NPs, suggesting that the ferric nitrate-based dealloying reaction only dissolves Ag (FIG. 4). This synthetic strategy led to the production of DIPs in a yield of about 95% (FIG. 3, L). The d-spacing of the adjacent lattice fringes of the DIPs was 0.235 nm, and their selected-area electron diffraction (SAED) was ring-like; the former corresponded to the (111) planes of a face-centered cubic structure while the latter was indicative of polycrystallinity (FIG. 3, M).

Figure 7:
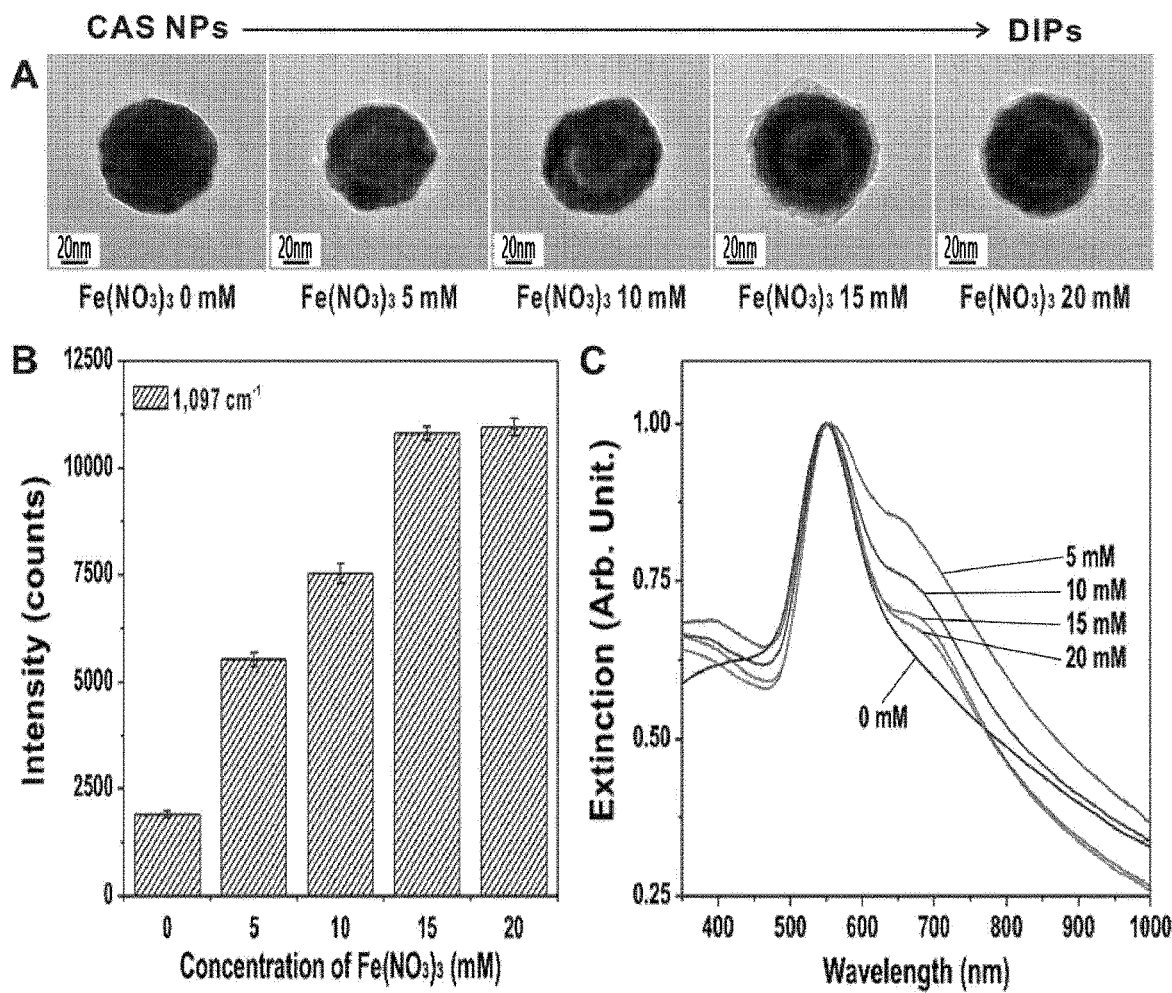
FIG. 7 shows drawings illustrating the changes in the structure and optical properties of DIPs according to the dealloying reaction.

To confirm the evolution of the intra-nanogap, the structural changes were monitored as the CAS NPs transformed into DIPs through the dealloying reaction while increasing the amount of $Fe(NO_3)_3$ added (FIG. 7). The mechanism proposed to explain the formation of the intra-nanogap structure is shown in FIG. 3A (see dotted box). When the $Fe(NO_3)_3$ solution was injected into the CAS NPs, the Ag atoms near the shell surface began to dissolve due to the $Fe(NO_3)_3$ (the solid line in a schematic diagram of the proposed mechanism), and the $Fe(NO_3)_3$ penetrated the CAS NPs through the Ag-etched sites. As the dealloying reaction progressed, pinhole-like vacancies (the black dotted open circles in the middle of the schematic diagram of the proposed mechanism) generated at the Ag-etched sites diffused inward (the solid line in the middle of the schematic diagram of the proposed mechanism), while metal atoms (mainly Ag atoms) diffused outward due to the nanometer-scale Kirkendall effect. In the case of a Au—Ag alloy system, the diffusion of Ag in Au is faster than that of Au in Ag, and thus, the net flux of the metals (Au and Ag) is mainly dependent on the diffusion rate of Ag. This resulted in a net flux of vacancies from the shell surface to the Au core. Therefore, the diffused Ag atoms were continually removed by the $Fe(NO_3)_3$ (the gray dotted lines in the middle of the schematic diagram of the proposed mechanism). Meanwhile, Au atoms diffused to a lesser degree and were interconnected with each other to minimize their surface energy. As this reaction continued, the accumulated vacancies near the Au core eventually resulted in the formation of a nanogap, while the interconnected Au atoms formed a dense shell. Similarly to the proposed mechanism, when $Fe(NO_3)_3$ (5 mM) was used in a small amount, the Ag atoms were partially etched and an incomplete intra-nanogap was formed. However, when $Fe(NO_3)_3$ was used in a large amount (>15 mM), the number of dissolved Ag atoms was higher (10 mM) and an intra-nanogap was formed uniformly (FIG. 7).

Figure 8:
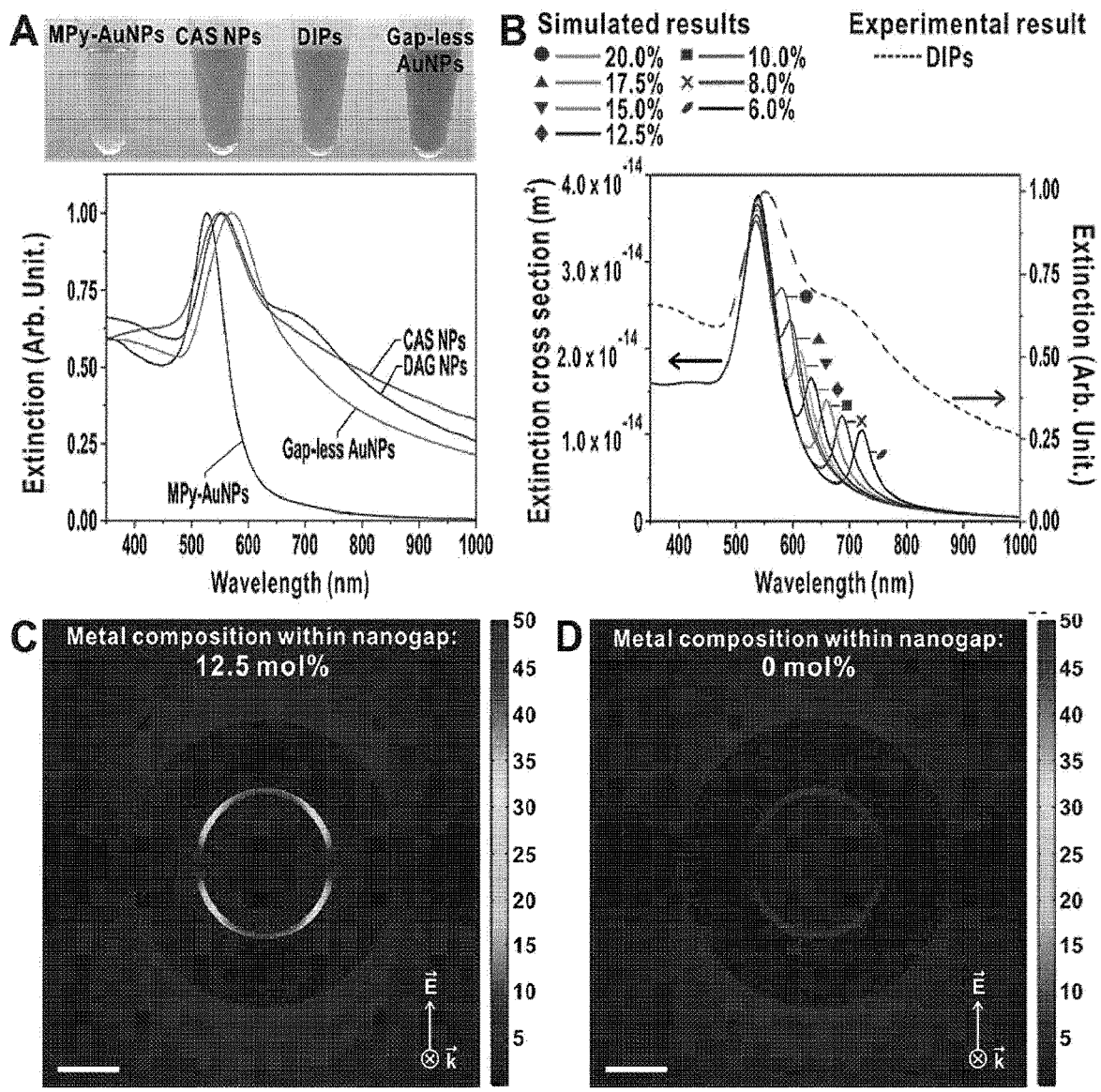
FIG. 8 shows drawings illustrating the experimental UV-Vis spectrum of NPs and the theoretical calculation of DIPs.
Figure 9:
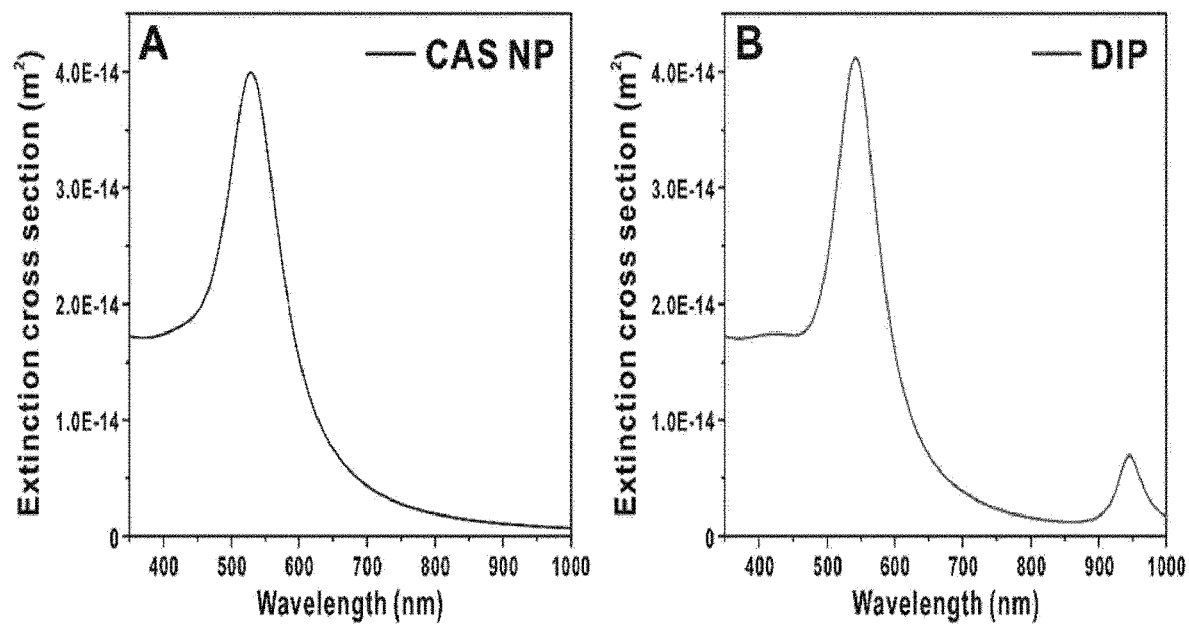
FIG. 9 shows simulated extinction spectra of as-synthesized NPs, in which, in FIG. 9, A shows the results of CAS NPs and B shows the results of DIPs. The theoretical calculations were performed using the Mie theory. The structural data used (average particle size, intra-nanogap size, shell thickness, and atomic composition) for the as-synthesized NPs are shown in FIG. 1 and Table 1. The background and intra-nanogap regions were modeled as water having a refractive index of 1.33. A new resonance peak was observed at about 950 nm only in the case of DIPs, indicating the generation of a new plasmonic mode due to the intra-nanogap.

Due to the morphological differences between the structures with a nanogap (DIPs) and without a nanogap (CAS NPs and gapless AuNPs), the UV-Vis spectra of these structures were also different (FIG. 8). Further, as shown in FIG. 8, A, with the formation of the shell structure, the color of the particle solution changed from pink (MPy-AuNPs) to dark pink (CAS NPs), then to blue-violet (DIPs), and finally to red-violet (gapless AuNPs). Further, the extinction peaks of the NPs with the shell structure were red-shifted compared to those of the shellless NPs ($\lambda$=528 nm, 549 nm, 554 nm, and 571 nm for the MPy-AuNPs, CAS NPs, DIPs, and gapless AuNPs, respectively). However, in the case of NPs with the intra-nanogap (DIPs), a new extinction shoulder peak was observed at about 700 nm. To elucidate the origin of this plasmonic peak from DIPs and to study the optical properties of the nanogap region, a computational simulation was performed based on the Mie theory. In this model, metal residues exist and are randomly distributed in the intra-nanogap region, and they partially interconnect the core and the shell. The intra-nanogap region was modeled as a mixture of metal residues and water, and the effective dielectric function of the gap region was calculated using the Smith approach that describes metallic behavior of mixtures with a low metallic volume fraction. When an intra-nanogap filled with water was formed inside of an NP, a new extinction peak appeared at a longer wavelength (about 950 nm) (FIG. 9). However, when an intra-nanogap region was filled with a mixture of metal residues and water, the resonance peak was blue-shifted to a shorter wavelength region from a longer wavelength region by changing the optical/physical state (e.g., effective dielectric function) of the nanogap. In addition, the resonance peak was continuously red-shifted to a longer wavelength as the metal composition in the nanogap decreased (FIG. 8, B). This trend was consistent with the changes in the UV-Vis spectra of DIPs according to different degrees of the dealloying reaction (FIG. 7). Since the degree of etching for each DIP in a solution varies slightly, the broadened shoulder peak from the experimental result can be explained by the superposition of UV-Vis spectra of DIPs having different metal compositions in the nanogap. FIG. 8C shows the calculated near-field EM field distribution of the DIPs containing 12.5 mol % of metal residues within the nanogap. Unlike the DIPs with a water-filled intra-nanogap (FIG. 8D), the DIPs with a metal residue-filled nanogap generated a highly enhanced EM field, indicating that the metal residues within the intra-nanogap play an important role in EM field enhancement.

SERS Analysis of DIPs in Solution

Figure 10:
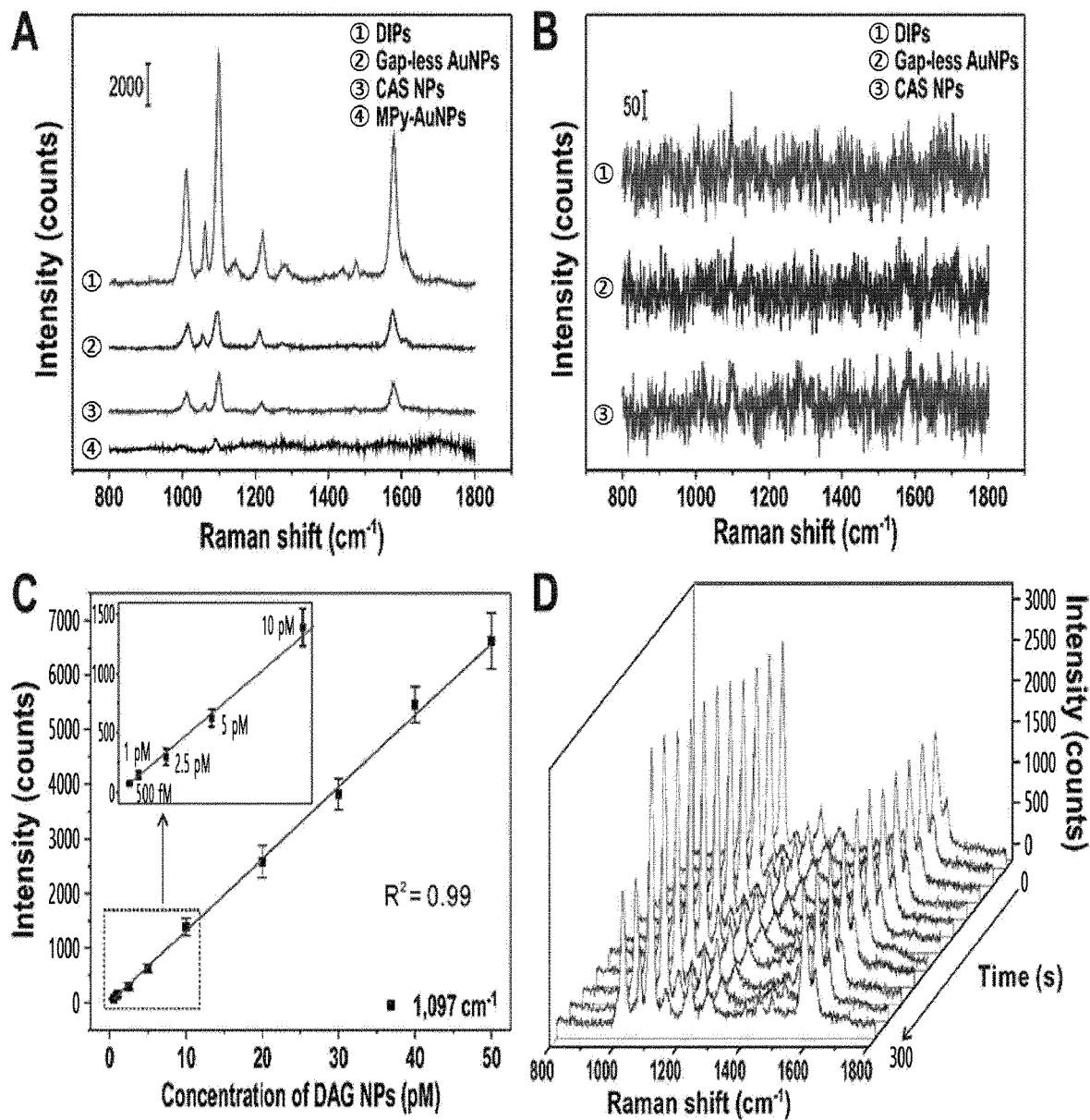
FIG. 10 shows drawings illustrating nanostructure, Raman dye position, particle concentration, and time-dependent SERS properties of as-synthesized NPs in a solution state, in which in FIG. 10, A shows SERS spectra of the as-synthesized NPs in a solution state (in which the Raman dye molecules (4-MPy) were attached to the Au core surfaces); B shows solution-based SERS spectra of 4-MPy-modified NPs (all of the dyes were modified to particle surfaces); C shows a graph illustrating the particle concentration-dependent changes in SERS signal intensity with DIPs (500 fM to 50 pM; 1,097 cm$^{-1}$); and D shows time-dependent profiles of DIPs. All of the spectra were obtained using a 633 nm laser (4 mW laser power) with an exposure time of 10 seconds. Particle concentrations used were 100 pM in A and B of FIG. 10, and 20 pM in D of FIG. 10.

Then, the solution-state SERS signals obtained from the as-synthesized NPs were compared with respect to the fingerprint peak at 1,097 $cm^{-1}$ (FIG. 10, A). Compared to the SERS signal intensity of the shellless AuNPs (MPy-AuNPs), those of the CAS NPs, gapless AuNPs, and DIPs were about 8.6, 7.7, and 50 times higher, respectively. In this case, Raman reporter molecules (4-MPy) were positioned in the intra-nanogap region. Both types of the nanogapless NPs (CAS NPs and gapless AuNPs) showed a similar increase in the SERS intensity. Thus, it was confirmed that the intra-nanogap can ensure a remarkably enhanced SERS signal and that the composition of the metallic phase has only a minor effect on the SERS phenomenon. To further confirm the role of the intra-nanogap on SERS enhancement, the Raman reporter molecules (4-MPy) were placed on the outermost shell surface instead of the Au core surface (FIG. 10, B). Regardless of the presence of an intra-nanogap, all of the similarly sized NPs (CAS NPs, gapless AuNPs, and DIPs) showed similar SERS signals, which were very weak. This result shows that the significantly stronger SERS enhancement was primarily attributable to the greater enhancement of the EM field in the intra-nanogap.

Figure 11:
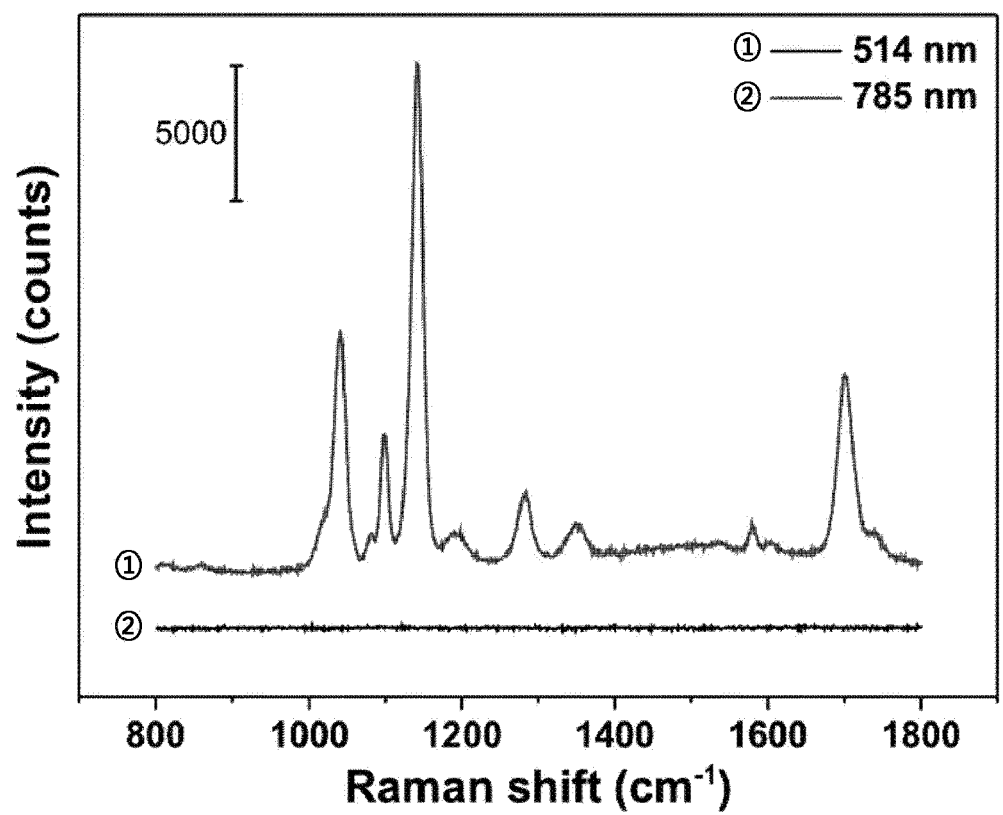
FIG. 11 is a diagram showing the extinction wavelength-dependent SERS spectra of DIPs. The spectra were obtained using the same particle concentration (100 pM). The exposure time was 10 seconds, and the laser powers used were 5 mW (514 nm) and 4 mW (785 nm), respectively.

Due to the highly enhanced EM field and the uniformly confined hot spots in the intra-nanogap, the SERS signal of the solution of the DIPs could be detected even at a very low concentration (500 fM), and a highly linear relationship ($R^2$=0.99) was shown between the NP concentration and the SERS signal intensity (FIG. 10, C). In addition, stable SERS signals were obtained during time-course measurements performed under continuous laser exposure (FIG. 10, D). These experimental results indicate that the DIPs generated highly robust and sustainable SERS signals due to the Raman molecules stably retained within a highly SERS-active narrow intra-nanogap. The properties of the DIPs, which enable generation of uniform and quantitatively reproducible SERS signals with high sensitivity, may possibly be exploited for biosensing/imaging. Further, the DIPs are highly responsive under excitation at a wavelength of 785 nm (FIG. 11); and thus, the DIPs may be suitable for use in in vivo, ex vivo, and in vitro SERS imaging as well as photothermal therapeutic probes. In contrast, the DIPs did not generate any detectable signal under excitation at a wavelength of 514 nm (FIG. 11). Since the near-field enhancement of the SERS effect is determined by the plasmonic excitation mode near the resonance peak, the 514 nm laser, whose wavelength is quite different from that corresponding to the near-field resonance peak induced by the plasmonic excitation mode of the intra-nanogap, could not generate a sufficiently strong EM field in the interior nanogap region.

Single-Particle-Level SERS Analysis of DIPs

Figure 12:
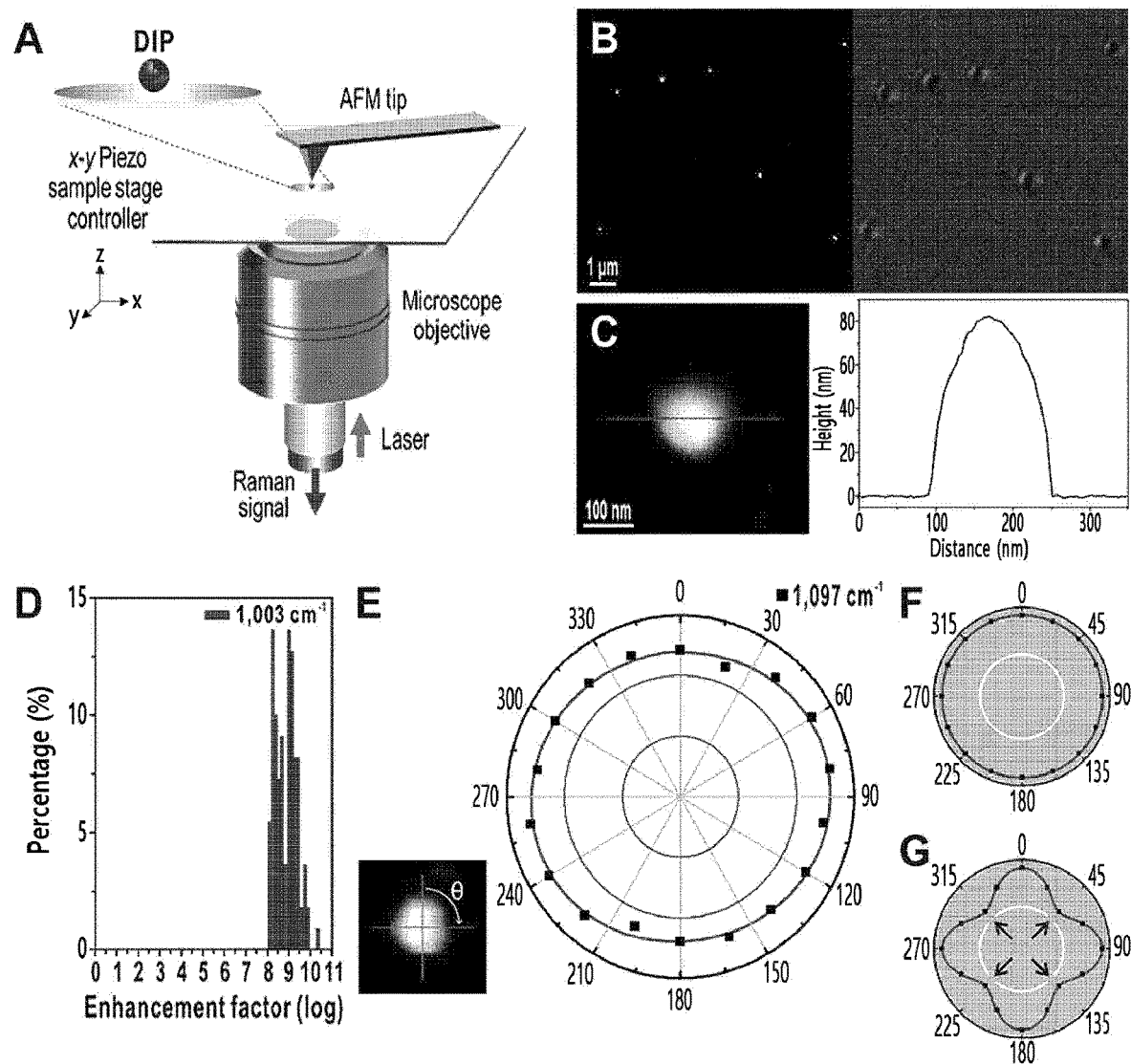
FIG. 12 shows drawings illustrating the AFM-correlated Raman spectroscopy-based single-particle mapping analysis, SERS enhancement factor (EF) distribution, and polarization-resolved SERS plot for DIPs, in which, in FIG. 12, A shows a schematic diagram illustrating the instrument setup used for AFM-correlated single-particle Raman spectroscopy; B shows images illustrating the morphological matching of an AFM image (left) and a Rayleigh scattering image (right) for DIPs; C shows a magnified AFM image of a single DIP (left) and a height profile across the NP (right, along the solid line in the AFM image); D shows a graph illustrating the distribution of SERS EF values at 1,003 cm$^{-1}$ from individual DIPs (analysis of 110 particles, in which EF values indicate a narrow distribution of large SERS EFs (90.0% and 97.3% particle populations were distributed in a range of from $1.1 \times 10^8$ to $2.5 \times 10^9$ and from $1.1 \times 10^8$ to $5.3 \times 10^9$, respectively) and all of the analyzed particles showed the EFs of $1.1 \times 10^8$ or greater); E shows a single-particle polarization-resolved plot at 1,097 cm$^{-1}$ with respect to the rotation angle (θ) of the SERS intensity; and F and G each show a calculated polarization-resolved plot of the EM field in the intra-nanogap region with respect to a rotation angle for DIPs and Au-NNPs, respectively. Theoretical calculations were performed using the finite element method with COMSOL, and the maximum values of the EM field enhancement at each rotation angle were plotted. The arrows in G of FIG. 12 represent Au nanobridges.

To more specifically examine the optical properties of the DIPs, an analysis of the SERS spectrum of the DIPs was performed at the single-particle level using an atomic force microscopy (AFM)-correlated nano-Raman instrument (FIG. 12, A). To obtain the SERS spectra of the individual DIPs, first, the end of the AFM tip was accurately matched with the focal spot of the objective lens. Then, the AFM topographical image and the Rayleigh scattering image were simultaneously obtained from the same particle (FIG. 12, B). The representative tapping-mode AFM image (10×10 µm$^2$) showed that the individual DIPs were well dispersed and did not overlap in the laser exposure focal spot (about 250 nm). Further, high-magnification AFM images confirmed that the DIPs were in a spherical shape, and their height profiles were consistent with their overall size as determined from the TEM images (FIG. 12, C). The SERS spectra of 110 individual DIPs were measured, and the enhancement factor (EF) values for the fingerprint peak at 1,003 cm$^{-1}$ were calculated.

FIG. 12, D shows a distribution diagram of the EF values of the individual DIPs (110 particles were measured). The individual NPs exhibited detectable high-intensity SERS signals, and the EF values of the DIPs showed a narrow distribution where 90.0% of the population was distributed between $1.1 \times 10^8$ and $2.5 \times 10^9$. Further, 97.3% of the population was distributed between $1.1 \times 10^8$ and $5.3 \times 10^9$. Moreover, the EF values were as high as $2.1 \times 10^{10}$ in some cases. Overall, all of the particles generated EFs of $\geq 1.1 \times 10^8$. The narrow distribution of the EF values results from the uniformly confined intra-nanogap and the highly precise synthesis of the targeted structure in a high yield. Therefore, such structures with a nanogap may be considered to be used as reproducible and reliable SERS probes. The EF values of DIPs were conservatively underestimated by assuming that the maximum number of 4-MPy molecules were uniformly packed on the AuNP core surface. In addition, non-resonant Raman dyes (4-MPy) with a small cross-section were used in the present invention. The EF values of the DIPs were $10^2$ to $10^3$ times higher than those with other nanostructures reported previously for the same Raman dye molecule (4-MPy). It is accepted that an EF of $10^6$ to $10^8$ could be sufficient for single-molecule detection. In this respect, the as-synthesized DIPs that generate very strong SERS signals with high sensitivity can be used as SERS probes in various analytical applications. The present inventors have investigated the incident laser polarization-dependent SERS characteristics of the DIPs at the single-particle level (FIG. 12, E). In the case of anisotropic or assembled nanostructures, the optical properties are dependent on the geometric configuration and laser polarization direction. In contrast, regardless of the polarization direction of the incident laser, the DIPs exhibited stable and uniform SERS signals due to the symmetrically distributed hot spots within the intra-nanogap. This polarization-independent property also makes the DIPs suitable for use as highly reliable, quantitative analytical probes. In the early stages of the synthesis of Au-NNPs with the nanobridges that connect a Au core and a Au shell, the extinction spectrum showed a new plasmonic resonance peak at about 680 nm, which is caused by the anisotropically branched budding structures on DNA-modified Au cores. In contrast, a new extinction peak was not observed during the synthesis of the CAS NPs (FIG. 5). These results suggest that the proposed co-reduction synthesis process forms the shell structures filled with a mixture of Au and Ag atoms, but does not form relatively large clusters such as Au branched budding structures. In addition, this suggests that unlike Au-NNPs, the intra-nanogap of DIPs consists of randomly distributed metal residues that can form a symmetrically distributed EM field within the intra-nanogap (FIG. 12, F and G).

DNA Assays with DIPs

Figure 13:
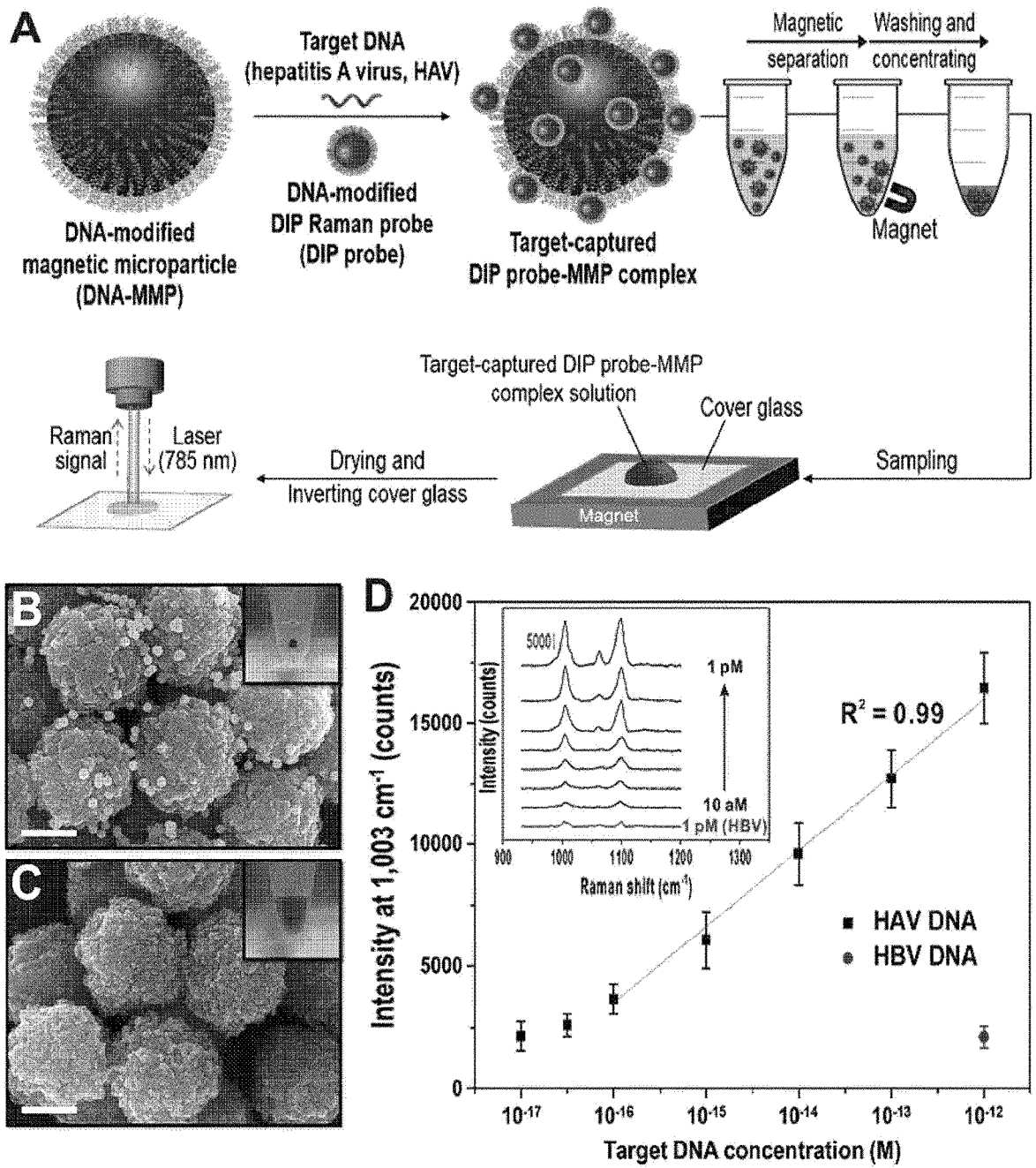
FIG. 13 shows drawings illustrating a SERS-based ultrasensitive DNA detection assay using DNA-functionalized DIPs, in which, in FIG. 13, A shows a schematic diagram illustrating a SERS-based ultrasensitive DNA detection assay using DNA-modified DIP nanoprobes by sandwich-capture of DNA-modified magnetic microparticles and target DNA; B and C each show an SEM image of a target DNA-specific sandwich hybridization complex (a target-captured DIP probe-MMP complex) formed using different linker DNA [B: complementary sequence DNA (HAV); C: non-complementary sequence DNA (HBV)], in which each inset shows the color of an assay solution under an external magnetic field after DNA sandwich hybridization (the scale bars are 500 nm); and D shows a graph illustrating the results of a SERS-based DNA detection assay using DNA-modified DIPs, in which the SERS intensities at 1,003 cm$^{-1}$ were measured at different concentrations of HAV DNA (10 aM to 1 pM) and HBV DNA (1 pM). The inset shows the change in the SERS spectra according to the concentration of the target DNA. All of the spectra were obtained with the acquisition time of 5 seconds using a 785 nm excitation laser (2 mW laser power). The SERS intensities were obtained and averaged with consecutive accumulation of five measurements for each concentration.

To test the potential of DIPs to be used as SERS sensing bioprobes, SERS-based ultrasensitive DNA detection assays were performed using the NPs. For efficient capture and separation of target DNA, DNA-modified magnetic microparticles (DNA-MMPs) and DIP Raman probes (DIP probes) were used to detect the target DNA strands (hepatitis A virus DNA; HAV DNA), based on a typical sandwich-hybridization assay (FIG. 13, A). To confirm the formation of sandwich hybridization complexes (target-captured DIP probe-MMP complexes) and their ability to undergo target DNA-specific hybridization, hybridization assays were performed with complementary (HAV) and non-complementary (HBV) DNA sequences (FIG. 13, B and C). In the presence of complementary DNA, the solution turned colorless due to an external magnetic field applied thereto, indicating that sandwich hybridization complexes were formed (inset in FIG. 13, B). However, in the presence of non-complementary DNA, the solution retained the color even after the MMPs were collected using a magnet, suggesting that the DIP probes were not captured by the DNA-MMPs (inset in FIG. 13, C). Moreover, the formation of the sandwich hybridization complexes was clearly shown in the scanning electron microscopy (SEM) images (FIG. 13, B and C). These results indicate that the proposed DNA detection method with DIPs is suitable for use in DNA detection assays. FIG. 13, D shows the change in SERS intensity at 1,003 cm$^{-1}$ for varying concentrations of target DNA (HAV) solutions (10 aM to 1 pM, black squares). The SERS intensity quantitatively decreased with a decrease in the concentration of the target DNA over a wide range. In contrast, the intensity of the SERS signal was very low during control experiments in which the target DNA was replaced with non-complementary DNA (HBV) strands (1 pM, red circular dot). The limit of detection (LOD) was in a range of about 10 aM to about 100 aM, which is more sensitive compared to the DNA detection results with other nanostructures and methods by about 10- to 1,000-fold. In terms of synthetic yield, structural precision, SERS EF distribution, and SERS signal stability, and reproducibility, DIPs generated superior results over other SERS structures, thus making highly sensitive and quantitative DNA detection possible. These results indicate that the plasmonic DIPs prepared by the SID process can be used as SERS probes for target-selective, ultrasensitive, and quantitative analysis.

Targeted Cell Imaging with DIPs

Finally, SERS-based target-specific cell imaging was performed using surface-functionalized DIPs (FIG. 14, A). To confirm the integrin-targeting specificity of the DIPs, a cyclo(Arg-Gly-Asp-D-Phe-Lys) (c-(RGDyK), hereinafter denoted as "cRGD") peptide, which specifically binds to integrin $\alpha_v\beta_3$ (overexpressed in metastatic and endothelial tumor cells), was attached onto the surfaces of the DIPs. Then, the cRGD-functionalized DIPs were introduced into different cell lines (e.g., U87MG (high integrin $\alpha_v\beta_3$ expression) and MCF-7 (integrin $\alpha_v\beta_3$-negative)). Due to the high expression of integrin $\alpha_v\beta_3$ in the U87MG cells and its preferential binding affinity for cRGD peptide, strong SERS signals were observed in the integrin $\alpha_v\beta_3$-positive U87MG cells, indicating the target-specific binding and SERS imaging capabilities of the cRGD-functionalized DIPs (FIG. 14, B and D). In contrast, SERS signals were rarely detected in the integrin $\alpha_v\beta_3$-negative MCF-7 cells, indicating the excellent target selectivity of the cRGD-functionalized DIPs for SERS-based cell imaging (FIG. 14, C and D). The cRGD-functionalized DIPs steadily generated uniform SERS signals when they were continuously exposed by a laser for a long period of time (FIG. 14, E). DIPs produced more reliable and stronger SERS signals for cell imaging than AuNPs with a similar size (FIG. 14, F and G and FIG. 15). These results indicate that the SERS-based cell imaging could be performed using a low-power laser (400 μW) with DIPs for a short exposure time (one second for each pixel), which are essential for minimizing cell and tissue damage and a stable long-term cell imaging.

Conclusions

The present inventors have developed a selective-interdiffusive dealloying-based facile synthetic strategy for forming highly SERS-active Au—Ag NPs (DIPs) containing a uniformly confined intra-nanogap in a high yield (about 95%). This strategy is a very simple, cheap, and efficient method for preparing interlayer-free intra-nanogap particles without using modulating interlayer materials (e.g., DNA, a polymer, or a silica shell). It was confirmed that the intra-nanogap, as small as about 2 nm, was formed by selective Ag-etching and interdiffusion of Ag atoms from the Au—Ag alloy shell (SID fixation). Metal residues were randomly distributed inside the gap. The NPs with the intra-nanogap showed highly enhanced SERS signals compared to those of the shellless or nanogapless NPs with a similar size, due to the strong EM field generated in the intra-nanogap by a strong plasmonic coupling between the core and the shell. Further, the DIPs emitted robust, stable, and quantitatively reproducible SERS signals and exhibited highly enhanced and narrowly distributed EFs, where 97.3% of the particle population was distributed between $1.1\times10^8$ and $5.3\times10^9$. Significantly, all of the analyzed particles showed EFs of $\geq 1.1\times10^8$. The present inventors have developed an ultrasensitive DNA detection assay with DIPs for the detection of target concentrations in a range of 10 aM to 1 pM that can be clearly distinguished as the SERS signals from DNA-modified DIPs. In addition, it was confirmed that the cRGD-functionalized DIPs can efficiently target integrin-overexpressed cells and steadily generate uniform SERS signals when continuously exposed to a laser for a long period of time. DIPs facilitated SERS cell imaging with a low-power laser (400 μW) and a short exposure time (one second for each pixel), thus making it possible to minimize cell and tissue damage and enable stable long-term cell imaging (>30 minutes). The synthetic strategy using the SID process provides a new method for forming a plasmonic nanostructure with a nanogap or a strong plasmonic coupling, which does not require an interlayer between two nanostructures (e.g., a core and a shell). DIPs show a potential as a strong, controllable, and quantitative SERS probe with a narrow distribution of high EFs without the dependence of a laser polarization direction, and DIPs can resolve the long-standing issues with respect to SERS signal reproducibility, reliability, and quantification capability. Finally, the results with respect to DNA detection and cell imaging using biofunctionalized DIP probes confirm and provide the opportunities for the use of the SERS probes in sensitive, selective biosensing, bioimaging, and theranostic applications with high reliability.

The invention claimed is:

1. A method for preparing core-gap-shell nanoparticles having a hollow space between a core and a shell, in which a Raman-active material is disposed, comprising:
   a first step of preparing first metal core particles, a surface of which is modified with the Raman-active material;
   a second step of adding solutions, which comprise a second metal precursor, a base, and a third metal precursor, respectively, and a solution of a reducing agent to the surface-modified first metal core particles to form an alloy shell of the second metal and the third metal to form nanoparticles of the first metal core, the surface of which is modified with the Raman-active material, and an alloy shell comprising the second metal and third metal; and
   a third step of dealloying by selectively removing the second metal from the alloy shell by treating the nanoparticles formed in the second step with a second metal etchant;
   wherein the first metal has a higher reduction potential compared to the second metal.

2. The method of claim 1, further comprising a step of treating the first metal core particles, the surface of which is modified with the Raman-active material, with a polymer solution having a functional group that has a higher binding affinity for the second metal compared to the third metal, before the second step.

3. The method of claim 2, wherein the polymer solution comprises polyvinylpyrrolidone.

4. The method of claim 1, wherein the first metal and the third metal are both gold and the second metal is silver.

5. The method of claim 4, wherein the second metal etchant is ferric nitrate ($Fe(NO_3)_3$).

6. The method of claim 1, wherein in the dealloying of the third step, second metal atoms on an outer surface of the shell begin to dissolve due to an etchant, and as a result, pinhole-like vacancies are formed, through which the etchant diffuses into the shell and selectively removes the second metal inside of the shell, and thereby a gap in the form of a hollow space is formed between the core and the shell.

7. The method of claim 1, wherein the hollow space has a height of at least about 2 nm.

8. The method of claim 1, further comprising functionalizing at least a portion of the core-gap-shell nanoparticles to provide functionalized core-gap-shell nanoparticles.

* * * * *

SEQUENCE LISTING

```
<160> NUMBER OF SEQ ID NOS: 4

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HAV 1 modified on magnetic bead

<400> SEQUENCE: 1
agaaagagga gttaa                                                      15

<210> SEQ ID NO 2
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: HAV 2 modified on DIPs

<400> SEQUENCE: 2
tccatgcaac tctaa                                                      15
```

```
<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: complementary DNA_HAV

<400> SEQUENCE: 3
ttagagttgc atggattaac tcctctttct                                    30

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: non-complementary DNA_HBV

<400> SEQUENCE: 4
ttggctttca gttatatgga tgatgtggta                                    30
```